United States Patent [19]
Tsuji et al.

[11] Patent Number: 5,218,109
[45] Date of Patent: Jun. 8, 1993

[54] STEROID COMPOUNDS

[75] Inventors: Jiro Tsuji, Okayama; Takashi Takahashi, Tokyo; Masao Tsuji, Kurashiki; Naoshi Nakagawa, Kurashiki; Tetsuo Takigawa, Kurashiki, all of Japan

[73] Assignee: Kuraray Co., Ltd., Kurashiki, Japan

[21] Appl. No.: 465,222

[22] PCT Filed: Sep. 28, 1988

[86] PCT No.: PCT/JP88/00988
§ 371 Date: Mar. 5, 1990
§ 102(e) Date: Mar. 5, 1990

[87] PCT Pub. No.: WO90/00560
PCT Pub. Date: Sep. 28, 1988

[30] Foreign Application Priority Data
Jul. 5, 1988 [JP] Japan .................. 63-168193

[51] Int. Cl.$^5$ .................. C07J 43/00; C07J 51/00; C07J 9/00; C07J 17/00
[52] U.S. Cl. .................. 540/4; 540/113; 540/114; 552/505; 552/582; 552/653
[58] Field of Search .............. 552/505, 553, 653, 582; 540/4, 113, 114

[56] References Cited

U.S. PATENT DOCUMENTS

| | | | |
|---|---|---|---|
| 4,193,921 | 3/1980 | Furst et al. | 552/653 |
| 4,260,804 | 4/1981 | DeLuca et al. | 552/653 |
| 4,310,467 | 1/1982 | Batcho et al. | 552/653 |
| 4,407,754 | 10/1983 | Barner et al. | 552/653 |

FOREIGN PATENT DOCUMENTS

| | | | |
|---|---|---|---|
| 0045524 | 2/1982 | European Pat. Off. | 552/582 |
| 0050325 | 4/1982 | European Pat. Off. | 552/653 |
| 0063678 | 11/1982 | European Pat. Off. | 552/653 |
| 0084199 | 7/1983 | European Pat. Off. | 552/653 |
| 0230600 | 8/1987 | European Pat. Off. | 552/653 |
| 2547199 | 5/1976 | Fed. Rep. of Germany | 552/653 |
| 131600 | 2/1981 | Japan . | |
| WO8501291 | 3/1985 | PCT Int'l Appl. | 552/653 |

OTHER PUBLICATIONS

Ikekawa, Medical Research Reviews, 7(3), 333-366 (1987).
Boris et al., Endocrinology of Calcium Metabolism, (Ravens Press, New York, 1982), pp. 297-320.

Primary Examiner—Robert T. Bond
Assistant Examiner—E. C. Ward
Attorney, Agent, or Firm—Oblon, Spivak, McClelland, Maier & Neustadt

[57] ABSTRACT

Steroid compounds of the following general formulas (I), (II) and (III) are provided:

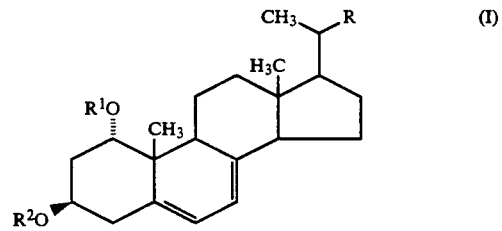

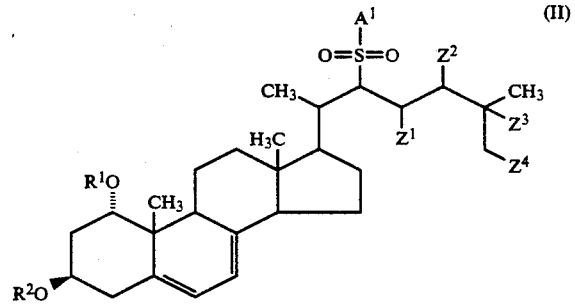

(Abstract continued on next page.)

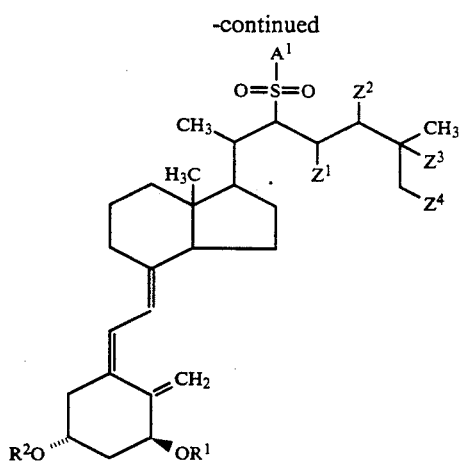
(III)

In the above formulas, $R^1$ and $R^2$ each is a hydrogen atom or a hydroxyl-protecting group, R is a group of the formula $-CH_2-X$ (in which X is a substituent such as a hydroxyl group), a carboxyl group or a protected carboxyl group, $A^1$ is an aryl group, a lower alkyl group or an aralkyl group, and $Z^1$, $Z^2$, $Z^3$ and $Z^4$ each is a hydrogen atom, a hydroxyl group or a protected hydroxyl group.

The above steroid compounds are useful as intermediates for the synthesis of vitamin $D_3$ derivatives having a hydroxyl group at the 1α-position.

3 Claims, No Drawings

STEROID COMPOUNDS

FIELD OF ART

This invention relates to novel steroid compounds.

The steroid compounds according to the invention are useful as intermediates for the synthesis of vitamin $D_3$ derivatives having a hydroxyl group at the 1α-position, for example 1α, 25-dihydroxyvitamin $D_3$ known to be useful in the treatment of diseases resulting from disturbances in calcium metabolism, such as chronic renal insufficiency, hypoparathyroidism, osteomalacia and osteoporosis, as well as 1α-hydroxyvitamin $D_3$, 1α, 23-dihydroxyvitamin $D_3$, 1α, 24-dihydroxyvitamin $D_3$, 1α, 23,25-trihydroxyvitamin $D_3$, 1α,24,25-trihydroxyvitamin $D_3$ and 1α, 25,26-trihydroxyvitamin $D_3$, which are known to have vitamin $D_3$-like activities.

PRIOR ART

The so-far known processes for the production of vitamin $D_3$ derivatives having a hydroxyl group at the 1α-position include, among others, the process for producing 1α-hydroxyvitamin $D_3$ using cholesterol as the starting material (cf. Japanese Laid-open Patent Application Kokai Nos. 62750/1973 and 95956/1974), the process for producing 1α, 25-dihydroxyvitamin $D_3$ via an intermediate, cholesta-1,5,7-trien-3-one-25-ol,

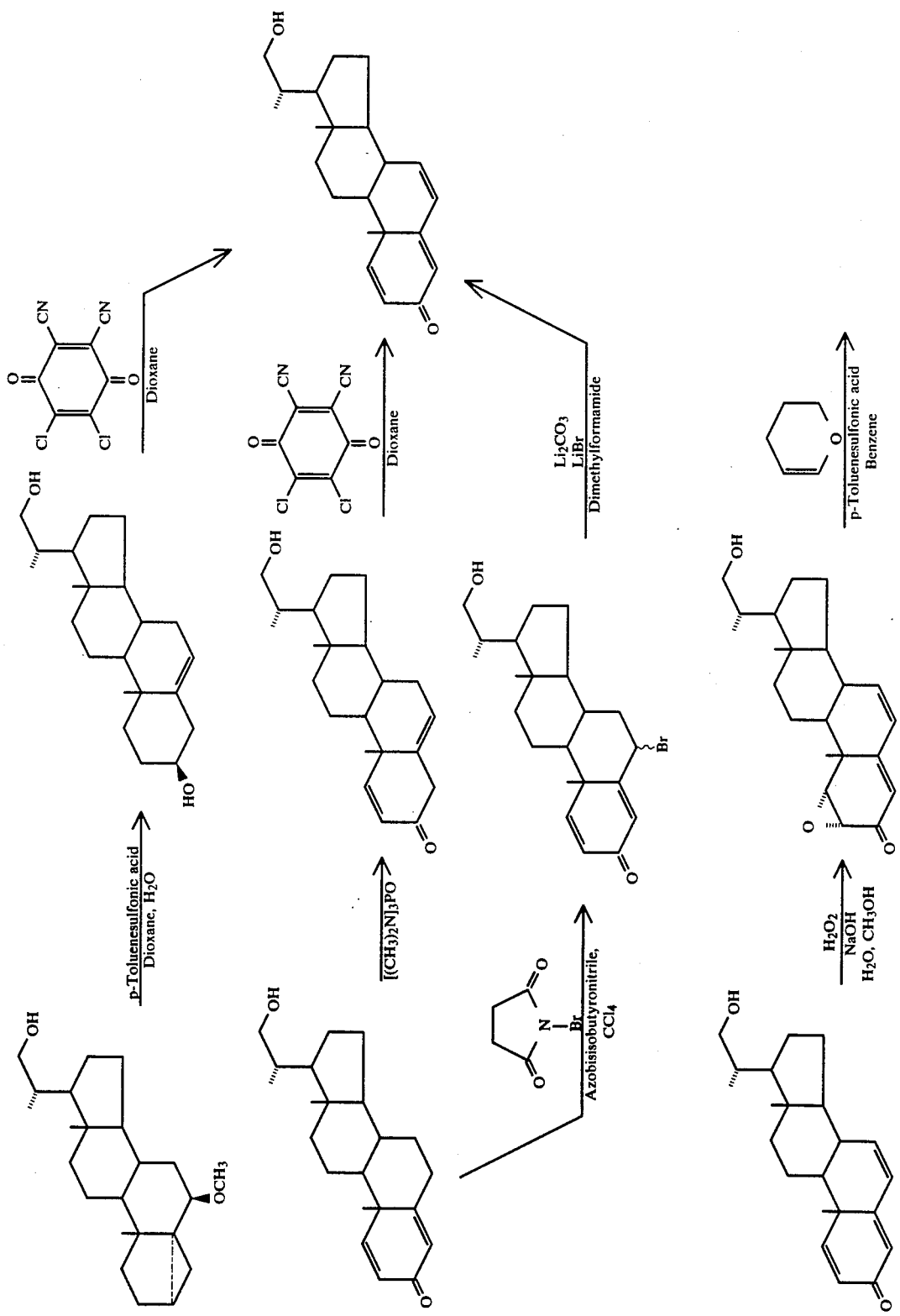

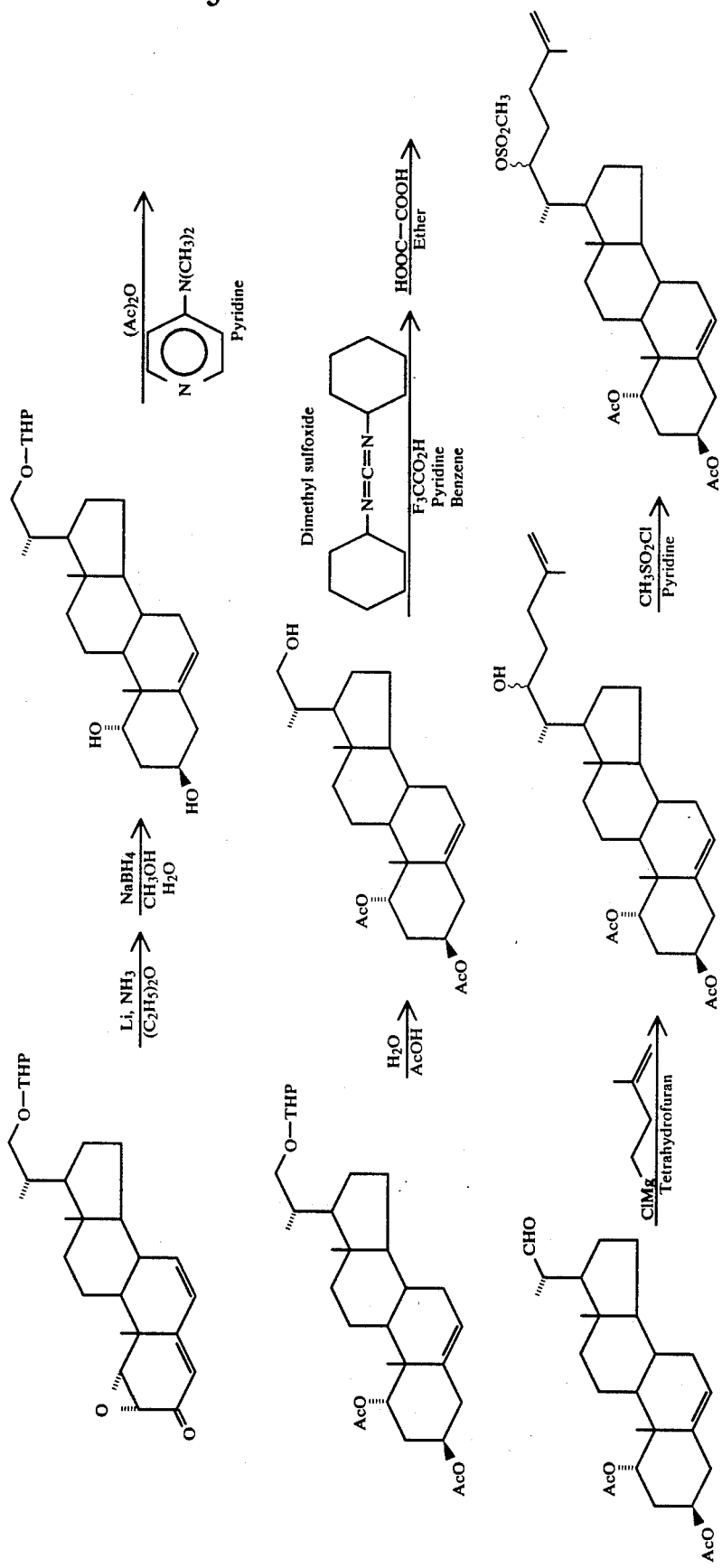

derived from cholesta-1,4,6-trien-3-one-25-ol (cf. Japanese Laid-open Patent Application Kokai No. 100056/1976), and the process for producing (24R)-1α, 24,25-trihydroxyvitamin $D_3$ which comprises irradiating (24R)-1α, 3β,24,25-tetrahydroxycholesta-5,7-diene with ultraviolet light in an inert organic solvent and isomerizing the resulting (24R)-1α, 24,25-trihydroxyprevitamin $D_3$ (cf. Japanese Laid-open Patent Application Kokai 108046/1986). A process is also known for the production of 1α, 25-dihydroxyvitamin $D_3$ (cf. Japanese Laid-open Patent Application Kokai No. 50152/1978) and this process uses, as an intermediate, such a pregnane derivative as (20S)-1α, 3β-diacetoxypregn-5-ene-20-carbaldehyde of the formula (i) shown below, which is derived from (20S)-21-hydroxy-20-methyl-6β-methoxy-3α,5-cyclo-5α-pregnane, (20S)-21-hydroxy-20-methylpregna-1,4-dien-3-one or the like. The latter process is schematically shown below.

converted to vitamin $D_3$ derivatives having a hydroxyl group at the 1α-position.

DISCLOSURE OF THE INVENTION

In accordance with the invention, the above object is accomplished by providing:

(1) Pregnane derivatives of the general formula

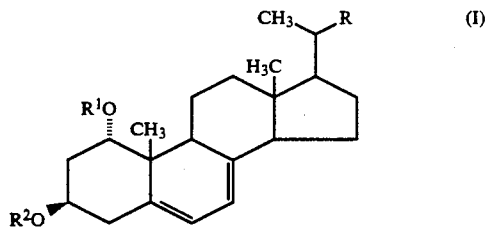

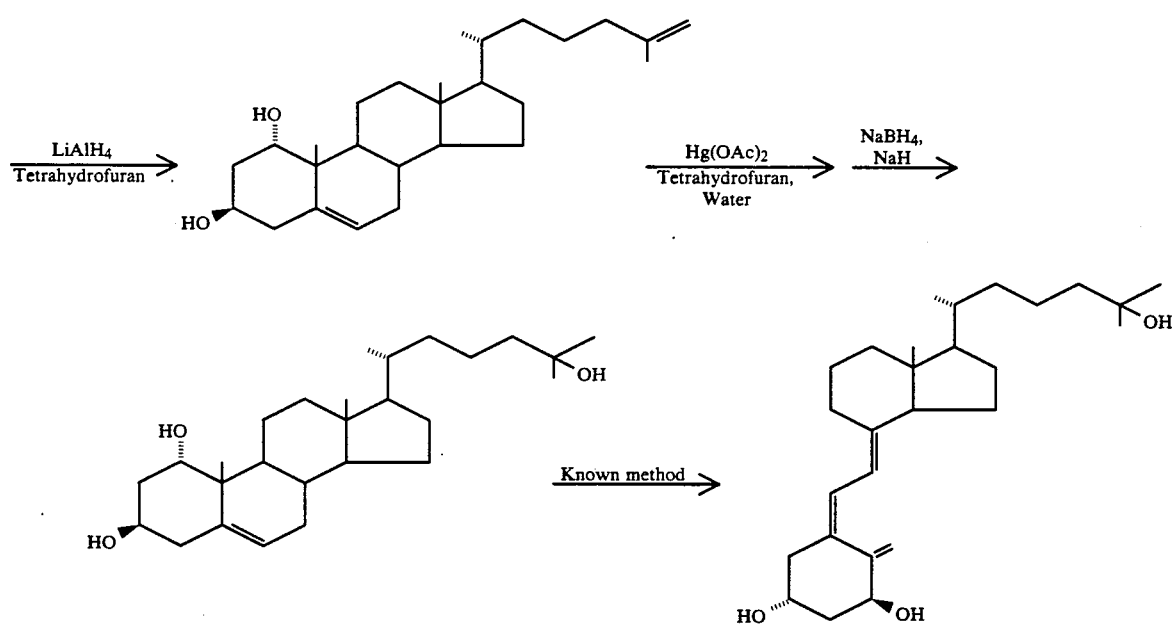

In the above formulas, THP means a tetrahydropyran-2-yl group, Ac means an acetyl group, ... (dotted line) indicates that the substituent is in the α-configuration, ▶ (wedge) indicates that the substituent is in the β-configuration and ~ (swung dash) indicates that the substituent is either in the α-configuration or in the β-configuration.

Furthermore, a process for producing 1α,25,26-trihydroxyvitamin $D_3$ from the above-mentioned (20S)-1α,3β-diacetoxypregn-5-ene-20-carbaldehyde of formula (i) is known (cf. Japanese Laid-open Patent Application No. 51447/1981).

While, as mentioned above, various processes are known for the production of vitamin $D_3$ derivatives having a hydroxyl group at the 1α-position, it would be desirable if many compounds become available as intermediates for the synthesis of such vitamin $D_3$ derivatives having a hydroxyl group at the 1α-position and, as a result, an appropriate process can be selected for the production thereof according to materials availability circumstances.

Accordingly, it is an object of the invention to provide various novel steroid compounds which can be wherein $R^1$ and $R^2$ each is a hydrogen atom or a hydroxyl-protecting group and R is a group of the formula —$CH_2$—X, a carboxyl group or a protected carboxyl group, X being a hydroxyl group, an acyloxyl group, a lower alkoxycarbonyloxyl group, a trisubstituted silyloxyl group, an alkoxymethoxyl group which may optionally be substituted, a benzyloxyl group which may optionally be substituted, a halogen atom, a substituted sulfonyloxyl group, a substituted sulfinyl group or a substituted sulfonyl group;

(2) Cholesta-5,7-diene derivatives of the general formula

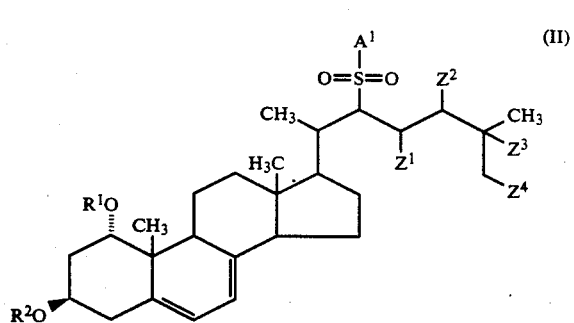

wherein $R^1$ and $R^2$ are as defined above, $A^1$ is an aryl group, a lower alkyl group or an aralkyl group and $Z^1$, $Z^2$, $Z^3$ and $Z^4$ each is a hydrogen atom, a hydroxyl group or a protected hydroxyl group; and (3) 9,10-Secocholesta-5,7,10(19)-triene derivatives of the general formula

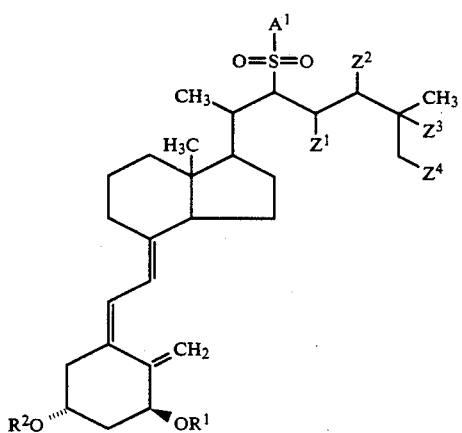

wherein $R^1$, $R^2$, $A^1$, $Z^1$, $Z^2$, $Z^3$ and $Z^4$ are as defined above.

The pregnane derivatives of general formula (I) may be roughly divided into two classes, namely 20-methyl-21-substituted pregnane derivatives of the general formula

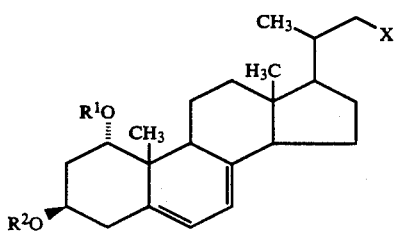

wherein $R^1$, $R^2$ and X are as defined above, and pregnane-20-carboxylic acid derivatives of the general formula

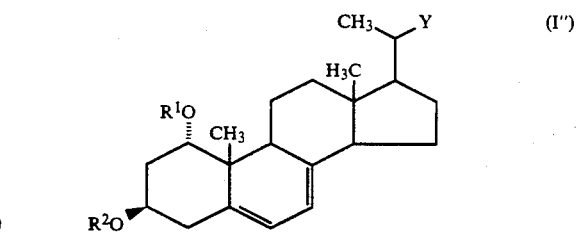

wherein $R^1$ and $R^2$ are as defined above and Y is a carboxyl group or a protected carboxyl group.

In the following, detailed mention will be made of $R^1$, $R^2$, R, $A^1$, X, Y, $Z^1$, $Z^2$, $Z^3$ and $Z^4$ appearing in the general formulas (I), (I'), (I''), (II) and (III) given above.

The hydroxyl-protecting group represented by $R^1$ and/or $R^2$ may be any of those protective groups which are generally used for the protection of hydroxyl groups provided that the intended purpose can be achieved. More specifically, there may be mentioned, as such groups, acyl groups, lower alkoxycarbonyl groups, trisubstituted silyl groups, and alkoxymethyl groups which may optionally be substituted, among others. Said acyl groups include acetyl, propionyl, butyryl, isobutyryl, valeryl, isovaleryl, pivaloyl, benzoyl, monochloroacetyl, trifluoroacetyl, etc., said lower alkoxycarbonyl groups include methoxycarbonyl, ethoxycarbonyl, isopropyloxycarbonyl, etc., said trisubstituted silyl groups include trialkylsilyl groups, such as trimethylsilyl, triethylsilyl, triisopropylsilyl and t-butyldimethylsilyl, diarylalkylsilyl groups, such as t-butyldiphenylsilyl, and so forth, and said alkoxymethyl groups which may optionally be substituted include, among others, alkoxymethyl groups, such as methoxymethyl and methoxyethoxymethyl, alkylsubstituted alkoxymethyl groups, such as 1-ethoxyethyl and 1-methoxy-1-methylethyl, and 2-oxacycloalkyl groups, such as tetrahydropyran-2-yl and tetrahydrfuran-2-yl.

The aryl group represented by $A^1$ is, for example, phenyl, p-tolyl, p-bromophenyl, p-methoxyphenyl, p-nitrophenyl or naphthyl, the lower alkyl group represented by $A^1$, is, for example, methyl, ethyl, propyl, isopropyl or butyl, and the aralkyl group represented by $A^1$ is, for example, benzyl, p-methylbenzyl, p-bromobenzyl or p-methoxybenzyl.

Referring to X, the acyloxyl group includes acetoxyl, propionyloxyl, butyryloxyl, isobutyryloxyl, valeryloxyl, isovaleryloxyl, pivaloyloxyl, benzoyloxyl, monochloroacetoxyl, trifluoroacetoxyl, etc., the lower alkoxycarbonyloxyl group includes methoxycarbonyloxyl, ethoxycarbonyloxyl, isopropyloxycarbonyloxyl, etc., the trisubstituted silyloxyl group includes, among others, trialkylsilyloxyl groups, such as trimethylsilyloxyl, triethylsilyloxyl, triisopropylsilyloxyl and t-butyldimethylsilyloxyl, and diarylalkylsilyloxyl groups, such as t-butyldiphenylsilyloxyl, the alkoxymethyoxyl group which may optionally be substituted includes, among others, alkoxymethoxyl groups, such as methoxymethoxyl and methoxyethoxymethoxyl, alkyl-substituted alkoxymethoxyl groups, such as 1-ethoxyethoxyl and 1-methoxy-1-methylethoxyl, and 2-oxacycloalkyloxyl groups, such as tetrahydropyran-2-yloxyl and tetrahydrofuran-2-yloxyl, the benzyloxyl group which may optionally be substituted includes benzyloxyl, p-nitrobenzyloxyl, triphenylmethoxyl, dimethoxytrityloxyl, etc., the halogen atom includes a fluorine atom, a chlorine atom, a bromine atom and an iodine atom, the substituted sulfonyloxyl group includes, among others, alkylsulfonyloxyl groups, such as methanesulfonyloxyl and ethanesulfonyloxyl, and arylsulfonyloxyl groups, such as benzenesulfonyloxyl, p-toluenesulfonyloxyl, p-bromobenzenesulfonyloxyl and p-nitrobenzenesulfonyloxyl, the hydrocarbylthio group includes, among others, alkylthio groups, such as methylthio, ethylthio, isopropylthio and t-butylthio, and arylthio groups, such as phenylthio, tolylthio, bromophenylthio, nitrophenylthio and methoxyphenylthio, the substituted sulfinyl group includes, among others, arylsulfinyl groups, such as phenylsulfinyl, tolylsulfinyl, trimethylphenylsulfinyl and methoxyphenylsulfinyl, alkylsulfinyl groups, such as methylsulfinyl, ethylsulfinyl and t-butylsulfinyl, and heterocycle-substituted sulfinyl groups, such as pyridylsulfinyl, and the substituted sulfonyl group includes, among others, arylsulfonyl groups, such as phenylsulfonyl, tolylsulfonyl, trimethylsulfonyl and methoxyphenylsulfonyl, alkylsulfonyl groups, such as methylsulfonyl, ethylsulfonyl and t-butylsulfonyl, and heterocycle-substituted sulfonyl groups, such as pyridylsulfonyl.

The protected carboxyl group represented by R and Y may be a carboxyl group protected by any of those groups which are generally used for protecting carboxyl groups provided that the protection purpose can be achieved. More specifically, there may be mentioned, as such groups, groups of the formula —COOR$^3$ in which R$^3$ is a lower alkyl group, an aryl group, an aralkyl group or a trisubstituted silyl group. Referring to R$^3$, the lower alkyl group is, for example, methyl, ethyl, propyl, isopropyl, butyl, isobutyl or t-butyl, the aryl group is, for example, phenyl, tolyl, bromophenyl or nitrophenyl, the aralkyl group is, for example, benzyl, nitrobenzyl, bromobenzyl or methoxybenzyl, and the trisubstituted silyl group is, for example, a trialkylsilyl group, such as trimethylsilyl, triethylsilyl, triisopropylsilyl or t-butyldimethylsilyl, or a diarylalkylsilyl group, such as t-butyldiphenylsilyl Referring to $Z^1$, $Z^2$, $Z^3$ and $Z^4$, the protected hydroxyl group may be a hydroxyl group protected by any of those groups which are generally used for protecting hydroxyl groups provided that it can satisfactorily achieve the purpose. More specifically, $Z^1$, $Z^2$, $Z^3$ and $Z^4$, each independently may be a group of the formula —OA$^2$ in which A$^2$ is an acyl group, a lower alkoxycarbonyl group, trisubstituted silyl group or an alkoxymethyl group which may optionally be substituted. As groups which two of $Z^1$, $Z^2$, $Z^3$ and $Z^4$ combinedly may form, there may be mentioned groups of the formula —O—A$^3$—O— in which A$^3$ is a methylene group which may optionally be substituted or a carbonyl group. Referring to A$^2$, the acyl group is, for example, acetyl, propionyl, butyryl, isobutytyl, valeryl, isovaleryl, pivaloyl, benzoyl, monochloroacetyl or trifluoroacetyl, the lower alkoxycarbonyl group is, for example, methoxycarbonyl, ethoxycarbonyl or isopropyloxycarbonyl, the trisubstituted silyl group is, for example, a trialkylsilyl group, such as trimethyl silyl, triethylsilyl, triisopropylsilyl or t-butyldimethylsilyl, or diarylalkylsilyl group, such as t-butyldiphenylsilyl, and the alkoxymethyl group which may optionally be substituted is, for example, an alkoxymethyl group, such as methoxymethyl or methoxyethoxymethyl, an alkyl-substituted alkoxymethyl group, such as 1-ethoxyethyl or 1-methoxy1-methylethyl, or an 2-oxacycloalkyl group, such as tetrahydropyran-2-yl or tetrahydrofuran-2-yl. Referring to A$^3$, the methylene group which may optionally be substituted is, for example, an alkylidene group, such as methylene, ethylidene, isopropylidene, cyclohexylidene, benzylidene or p-methoxybenzylidene, or an alkoxymethylene group, such as methoxymethylene or ethoxymethylene.

. The pregnane derivatives of general formula (I) can be produced, for example, by the following processes:

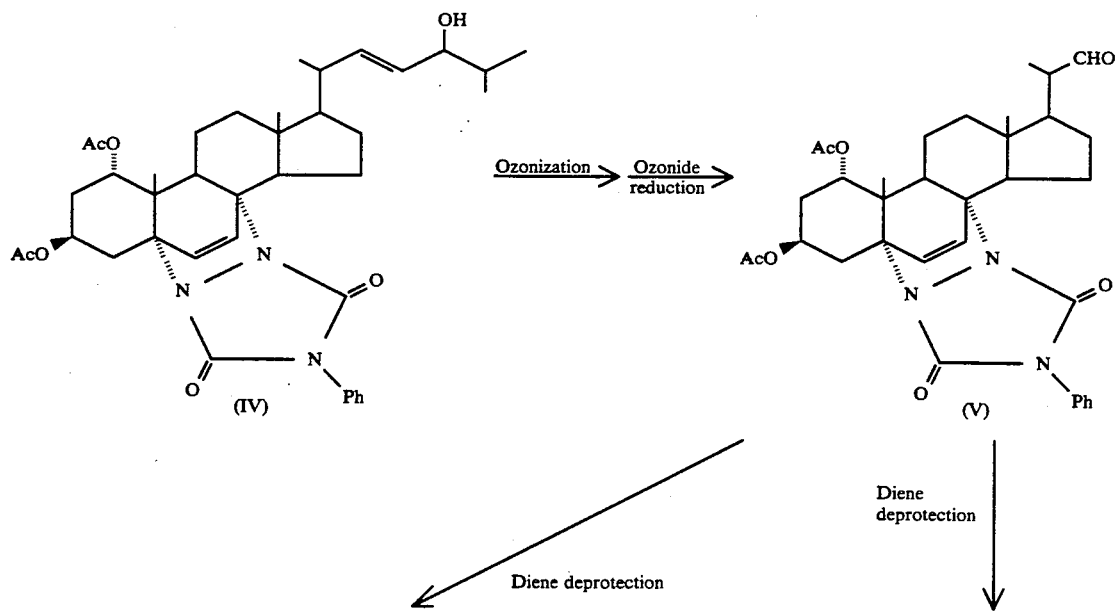

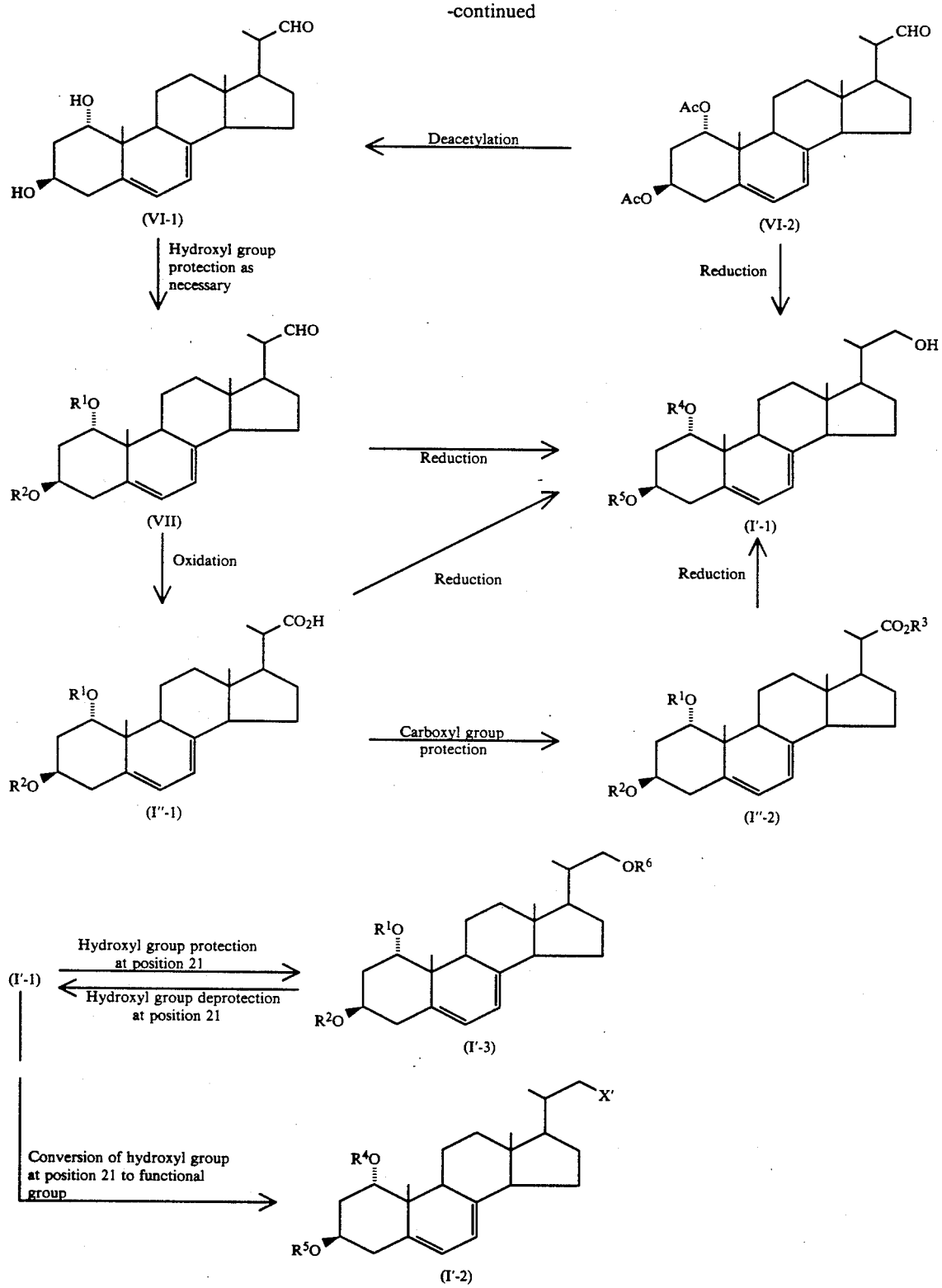

In the above formulas, R$^1$, R$^2$ and R$^3$ are as defined above, R$^4$ and R$^5$ each is a hydrogen atom or a hydroxyl-protecting group (e.g. an acyl group, a lower alkoxycarbonyl group, a trisubstituted silyl group, an alkoxymethyl group which may optionally be substituted, etc.), R$^6$ is a hydroxyl-protecting group, X' is a halogen atom, a substituted sulfonyloxyl group, a hydrocarbylthio group, a substituted sulfinyl group or a substituted sulfonyl group, Ac is an acetyl group and Ph is a phenyl group.

Among the compounds shown above, the compounds represented by the general formula (I'-1), (I'-2) or (I'-3) are included in the class of compounds of general formula (I'), while the compounds represented by the general formula (I''-1) or (I''-2) are included in the class of compounds of general formula (I'').

Hereinafter, the compounds represented by the formulas or general formulas (I'-1), (I'-2), (I'-3), (I''-1), (I''-2), (IV), (V), (VI-1), (VI-2) and (VII) given above are sometimes referred to briefly as follows:

| Formula or general formula | To be referred to as: |
|---|---|
| (I'-1) | 20-Hydroxymethylpregnane derivative (I'-1) or alcohol (I'-1) |
| (I'-2) | 20-Substituted-methylpregnane derivative (I'-2) |
| (I'-3) | Protected alcohol (I'-3) |
| (I''-1) | Pregnane-20-carboxylic acid derivative (I''-1) or carboxylic acid (I''-1) |
| (I''-2) | Pregnane-20-carboxylic acid derivative (I''-2) |
| (IV) | Compound (IV) |
| (V) | Aldehyde (V) |
| (VI-1) | Aldehyde (VI-1) |
| (VI-1) | Aldehyde (VI-2) |
| (VI-2) | Aldehyde (VII) |

Furthermore, the compounds of general formula (I''-2) are hereinafter sometimes referred to briefly, according to the atom or group represented by X', as follows:

| X' | To be referred to as: |
|---|---|
| Halogen atom | Halide (I''-2-1) |
| Substituted sulfonyloxyl | Sulfonate (I''-2-2) |
| Hydrocarbylthio | Sulfide (I'-2-3) |
| Substituted sulfinyl | Sulfoxide (I'-2-4) |
| Substituted sulfonyl | Sulfone (I'-2-5) |

The compounds of general formula (I'-3) in which $R^6$ is as given below are hereinafter sometimes referred to briefly, according to the hydroxyl protecting group $R^6$, as follows:

| $R^6$ | To be referred to as: |
|---|---|
| Acyl | Acyl ester (I'-3-1) |
| Lower alkoxycarbonyl | Carbonate (I'-3-2) |
| Trisubstituted silyl | Silyl ether (I'-3-3) |
| Alkoxymethyl which may optionally be substituted | Ether (I'-3-4) |

The compounds of general formula (I''-2) in which $R^3$ is as given below are hereinafter sometimes referred to briefly, according to the group $R^3$, as follows:

| $R^3$ | To be referred to as: |
|---|---|
| Lower alkyl, aryl or aralkyl | Ester (I'-2-1) |
| Trisubstituted silyl | Silyl ester (I'-2-2) |

The compounds of general formula (VII) in which $R^1$ and $R^2$ are as given below are hereinafter sometimes referred to briefly, according to $R^1$ and $R^2$, as follows:

| $R^1$ and $R^2$ | To be referred to as: |
|---|---|
| Acyl | Aldehyde (VII-1) |
| Lower alkoxycarbonyl | Aldehyde (VII-2) |
| Trisubstituted silyl | Aldehyde (VII-3) |
| Alkoxymethyl which may optionally be substituted | Aldehyde (VII-4) |

The compound (IV) can be prepared by the method of H. Sai et al. [cf. Chem. Pharm. Bull., 32, 3866–3872 (1984)].

The compound (IV) can be converted to the aldehyde (VI-1) or (VI-2) by selected ozonization of the side chain carbon-carbon double bond of the compound (IV) and reduction of the resulting ozonide to give the aldehyde (V), followed by deprotection to regenerate the 5,7-diene structure. The ozonization and reduction of the ozonide can be carried out in a conventional manner. Thus, ozonization is carried out, for example, by ozone gas passing through a solution of the compound (IV) with cooling, or by addition of a saturated solution of ozone prepared in advance to a solution of the compound (IV) with cooling. The reduction of the ozonide is carried out by addition of an appropriate reducing agent. The amount of ozone gas used is within the range of about 0.1 to 10 moles, preferably about 0.5 to 0.8 mole, per mole of compound (IV). This reaction is generally carried out in a solvent, such as methylene chloride or methanol which will not interfere with the reaction. The amount of the solvent used is within the range of about 10 to 200 parts per part of the compound (IV) by weight. The solvent may contain about 1%(v/v) of pyridine. Said ozonization reaction is generally carried out at 0° C. or below, preferably at a temperature within the range of about −50° C. to −100° C. The reducing agent to be used in the reduction of the ozonide is, for example, dimethyl sulfide or triphenylphosphine, and the amount of the reducing agent is within the range of about 1 to 50 moles per mole of compound (IV). The reduction of the ozonide is generally carried out at a temperature within the range of −100° C. to 30° C. In a preferred embodiment, said ozonization and ozonide reduction are performed by cooling a methylene chloride solution containing about 0.5 to 0.8 mole, per mole of compound (IV), of ozone and 1% of pyridine in a dry ice-acetone bath, adding this cooled solution to a solution of the compound (IV) with cooling in a dry ice-acetone bath, then adding, after confirming the disappearance of the blue color of ozone, about 20 moles, per mole of the compound (IV) used, of dimethyl sulfide, removing the dry ice-acetone bath, and allowing the temperature to rise to ambient temperature.

The thus-produced aldehyde (V) can be isolated and purified from the reaction mixture in the same manner as a conventional isolation and purification procedures taken in ordinary organic reactions. Thus, for example, the reaction mixture is washed in sequence with cold, diluted hydrochloric acid and an aqueous solution of sodium chloride, dried and concentrated, and the resulting residue is purified by recrystallization or chromatography, for instance, to give the aldehyde (V).

The aldehyde (V) can be converted to the aldehyde (VI-1) or (VI-2) by deprotecting the diene by a conventional method. This deprotection reaction is carried out by, for example, treating the aldehyde (V) with potassium hydroxide in ethanol, heating in dimethyl sulfoxide in the presence of potassium carbonate, or heating in collidine. In these reactions, the amount of the ethanol, dimethyl sulfoxide or collidine is within the range of about 5 to 200 parts per part of aldehyde (V) by weight. The amount of potassium hydroxide is in the range of about 10 to 500 moles, preferably 50 to 200 moles, per mole of aldehyde (V), and the amount of potassium carbonate is within the range of about 0.5 to 2 moles per mole of aldehyde (V). When treating the aldehyde (V)

with potassium hydroxide in ethanol to deprotect, the aldehyde (VI-1) is obtained as the product and, when heating in dimethyl sulfoxide in the presence of potassium carbonate or heating in collidine to deprotect, the aldehyde (VI-2) is obtained as the product. When the aldehyde (VI-1) is the desired product, it is easy and simple that the deprotection reaction is carried out by heating the aldehyde (V) under reflux in about 2N ethanolic potassium hydroxide solution containing about 100 moles of potassium hudroxide per mole of aldehyde (V) for about 1.5 hours, when the aldehyde (VI-2) is desired, by heating the aldehyde (V) in about 50 parts of dimethyl sulfoxide per part weight of aldehyde (V) by weight in the presence of about 1 mole of anhydrous potassium carbonate per mole of aldehyde (V) at about 120° C. for about 7 hours.

The aldehyde (VI-1) or aldehyde (VI-2) can be isolated and purified from the reaction mixture in the same manner as a conventional isolation and purification procedure used in ordinary organic reactions. Thus, for instance, the reaction mixture is cooled and poured into water, the resulting mixture is extracted with an organic solvent, such as ethyl acetate, the extract is washed with cold diluted hydrochloric acid, an aqueous solution of sodium bicarbonate and an aqueous solution of sodium chloride in that order, dried and concentrated, and the resulting residue is purified by recrystallization or chromatography, for instance, to give the aldehyde (VI-1) or aldehyde (VI-2).

The aldehyde (VI-2) thus obtained may be converted, if necessary, to the aldehyde (VI-1) by deacetylation of the acetoxyl groups at the positions 1α and 3β. The deacetylation reaction can be carried out in the same manner as an ordinary deacetylation reaction, namely by subjecting the aldehyde (VI-2) to solvolysis which is conducted by bringing the aldehyde (VI-2) into contact with water or alcohol in the presence of a basic substance. As the alcohol used in this solvolysis, there may be mentioned, for example, lower alcohols such as methanol and ethanol. Generally the amount of water or the alcohol used in the solvolysis reaction is within the range of about 2 to 2,000 moles per mole of the aldehyde (VI-2). Usable as the basic substance are, for example, metal alkoxides, such as sodium methoxide and sodium ethoxide, metal hydoxides, such as sodium hydroxide and potassium hydroxide, and metal carbonates, such as potassium carbonate and sodium carbonate. Generally the amount of the basic substance is within the range of about 0.05 to 10 moles, preferably about 0.1 to 5 moles per mole of the aldehyde (VI-2). This reaction is generally carried out in a solvent. The reactant water or alcohol may also be used as a solvent and it is also possible to use another solvent as an auxiliary solvent. Such auxiliary solvent should have an affinity for both of the reactant water or an alcohol and the aldehyde (VI-2) but should not interfere with the reaction. Typical example are methanol, ethanol, tetrahydrofuran and dioxane. Generally the amount of the solvent is within the range of about 5 to 200 parts per part of aldehyde (VI-2) by weight. The reaction is carried out generally at a temperature within the range of −10° C. to 100° C., preferably within the range of about 0° C. to 60° C. It is easy and simple that this solvolysis reaction is carried out by stirring the aldehyde (VI-2) in about 100 parts per part of aldehyde (VI-2) by weight, of methanol in the presence of about 5 moles per mole of aldehyde (VI-2), of potassium carbonate for 15 to 24 hours at ambient temperature.

The aldehyde (VI-1) can be isolated and purified from the reaction mixture in the same manner as conventional isolation and purification procedures used in ordinary organic reactions. Thus, for instance, the reaction mixture is cooled and poured into water, the resulting mixture is extracted with an organic solvent, such as ethyl acetate, the extract is washed with a cold diluted hydrochloric acid, an aqueous solution of sodium bicarbonate and an aqueous solution of sodium chloride, then dried and concentrated and the resulting residue is purified by recrystallization or chromatography, for instance, to give the aldehyde (VI-1).

The thus-produced aldehyde (VI-1) can be converted, if necessary, to an aldehyde of general formula (VII) in which $R^1$ and $R^2$ each is a hydroxyl-protecting group by protecting the hydroxyl groups at the positions 1α and 3β by a conventional method. In that case, it is also possible to first prepare a monoprotected diol by protecting one of the hydroxyl groups at the positions 1α and 3β and then protect the remaining free hydroxyl group to give an aldehyde of general formula (VII) in which $R^1$ and $R^2$ each is a hydroxyl-protecting group.

The aldehyde (VI-1) is converted to the aldehyde (VII-1) by treating the aldehyde (VI-1) with a carboxylic acid anhydride or a carboxylic acid halide in the presence of a basic substance. As the carboxylic acid anhydride to be used in this reaction, there may be mentioned acetic anhydride, propionic anhydride, butyric anhydride, trifluoroaceticanhydride, etc. As the carboxylic acid halide, there may be mentioned acetyl chloride, propionyl chloride, butyryl chloride, isobutyryl chloride, valeryl chloride, isovaleryl chloride, pivaloyl chloride, benzyl chloride, etc. Generally the amount of the carboxylic acid anhydride or the carboxylic acid halide used in this reaction is within the range of about 2 to 20 moles, preferably about 2.5 to 10 moles per mole of the aldehyde (VI-1). The basic substance to be used in this reaction includes, among others, organic bases, such as pyridine, triethylamine, diisopropylethylamine and diethylaniline, metal hydroxides, such as sodium hydroxide and potassium hydroxide, and metal hydrides, such as sodium hydride. Generally the amount of the basic substance used in this reaction is within the range of about 2 to 200 moles, preferably about 5 to 100 moles per mole of the aldehyde (VI-1). The reaction may also be carried out in the presence of an acylation catalyst, such as dimethylaminopyridine or pyrrolidinopyridine. Generally the amount of the acylation catalyst is within the range of about 0.05 to 0.2 mole per mole of the aldehyde (VI-1). The reaction is generally carried out in a solvent. The organic base may be used as a solvent and it is also possible to use, as an auxiliary solvent, a solvent, for example methylene chloride or tetrahydrofuran, which will not interfere with the reaction. In any case, generally the amount of the solvent is within the range of about 5 to 200 parts per part of aldehyde (VI-1) by weight. The reaction is generally carried out at a temperature within the range of about −20° C. to 100° C., preferably within the range of about 0° C. to 30° C.

The thus-produced aldehyde (VII-1) can be isolated and purified from the reaction mixture in the same manner as in conventional isolation and purification procedures used in ordinary organic reactions. Thus, for example, the reaction mixture is poured into ice water, the resulting mixture is extracted with an organic solvent, for example diethyl ether, the extract is washed in sequence with cold diluted hydrochloric acid, an aqueous solution of sodium bicarbonate and an aqueous solution of sodium chloride, then dried and concentrated, and the resulting residue is purified by recrystallization or chromatography, for instance, to give the aldehyde (VII-1).

The aldehyde (VI-1) can be converted to the aldehyde (VII-2) by treating the aldehyde (VI-1) with a chlorocarbonate ester in the presence of a basic substance. The chlorocarbonate ester to be used in the reaction is, for example, methyl chlorocarbonate, ethyl chlorocarbonate, allyl chlorocarbonate, trichloroethyl chlorocarbonate or phenyl chlorocarbonate. Generally the amount of the chlorocarbonate is within the range of about 2 to 50 moles, preferably 5 to 20 moles per mole of the aldehyde (VI-1). As the basic substance to be used in the reaction, there may be mentioned, among others, amines, such as pyridine, triethylamine, diisopropylethylamine and diethylaniline, metal hydroxides, such as sodium hydroxide and potassium hydroxide, and metal hyrides, such as sodium hydride. Generally the amount of the basic substance is within the range of about 2 to 200 moles, preferably about 5 to 100 moles per mole of the aldehyde (VI-1). The reaction may be carried out in the presence of an esterification catalyst, such as dimethylaminopyridine or pyrrolidinopyridine. Generally the amount of the esterification catalyst is within the range of about 0.05 to 0.2 mole per mole of the aldehyde (VI-1). This reaction is generally carried out in a solvent. The amine used as the basic substance, may serve also as a solvent. It is possible to use, as an auxiliary solvent, a solvent, such as methylene chloride or tetrahydrofuran, which will not interfere with the reaction. Generally the amount of the solvent is within the range of about 5 to 200 parts per part of the aldehyde (VI-1) by weight. The reaction is generally carried out at a temperature within the range of about $-20°$ C. to $100°$ C., preferably within the range of about $0°$ C. to $30°$ C.

The aldehyde (VII-2) thus produced can be isolated and purified from the reaction mixture in the same manner as conventional isolation and purification procedures used in ordinary organic reactions. Thus, for example, the reaction mixture is poured into ice water, the resulting mixture is extracted with an organic solvent, for example ether, the extract is washed in sequence with cold diluted hydrochloric acid, an aqueous solution of sodium bicarbonate and an aqueous solution of sodium chloride, then dried and concentrated, and the resulting residue is purified by recrystallization or chromatography, for instance, to give the aldehyde (VII-2).

The aldehyde (VI-1) can be converted to the aldehyde (VII-3) by treating the aldehyde (VI-1) with a trisubstituted silyl chloride in the presence of a basic substance. The trisubstituted silyl chloride to be used in the reaction may include, among others, trialkylsilyl chlorides, such as trimethylsilyl chloride, triethylsilyl chloride, triisopropylsilyl chloride and t-butyldimethylsilyl chloride, and diarylalkylsilyl chlorides, such as t-butyldiphenylsilylchloride. Generally the amount of the trisubstituted silyl chloride is within the range of about 2 to 50 moles, preferably about 5 to 20 moles per mole of the aldehyde (VI-1). As the basic substance used in the reaction, there may be mentioned, among others, amines, such as pyridine, triethylamine, diisopropylethylamine, diethylaniline and imidazole, metal hydroxides, such as sodium hydroxide and potassium hydroxide, and metal hydrides, such as sodium hydride. Generally the amount of the basic substance is within the range of about 2 to 200 moles, preferably about 5 to 100 moles per mole of the aldehyde (VI-1). This reaction is generally carried out in a solvent. The amine used as the basic substance, may serve also as a solvent. It is possible to use, as an auxiliary solvent, a solvent, such as methylene chloride, tetrahydrofuran of dimethylformamide, which will not interfere with the reaction. Generally the amount of the solvent is within the range of about 5 to 200 parts per part of the aldehyde (VI-1) by weight. The reaction is generally carried out at a temperature within the range of about $-20°$ C. to $100°$ C., preferably within the range of about $0°$ C. to $30°$ C.

The aldehyde (VII-3) thus produced can be isolated and purified from the reaction mixture in the same manner as conventional isolation and purification procedures used in ordinary organic reactions. Thus, for instance, the reaction mixture is poured into ice water, the resulting mixture is extracted with an organic solvent, for example ether, the extract is washed in sequence with cold diluted hydrochloric acid, an aqueous solution of sodium bicarbonate and an aqueous solution of sodium chloride, then dried and concentrated, and the resulting residue is purified by recrystallization or chromatography, for instance, to give the aldehyde (VII-3).

The aldehyde (VI-1) can be converted to the aldehyde (VII-4) by treating the aldehyde (VI-1) with a chloromethyl ether in the presence of a basic substance or by treating the aldehyde (VI-1) with a vinyl ether in the presence of an acid catalyst. The chloromethyl ether used in the reaction is, for example, chloromethyl methyl ether or methoxyethoxymethyl chloride, and the vinyl ether is, for example, ethyl vinyl ether, methyl isopropenyl ether, dihydropyran or dihydrofuran. Generally the amount of the chloromethyl ether or vinyl ether is within the range of about 2 to 50 moles, preferably about 5 to 20 moles per mole of the aldehyde (VI-1). As the basic substance used in the reaction, there may be mentioned, among others, amines, such as pyridine, triethylamine, diisopropylethylamine, diethylaniline and imidazole, and metal hydrides, such as sodium hydride. Generally the amount of the basic substance is within the range of about 2 to 200 moles, preferably about 5 to 100 moles per mole of the aldehyde (VI-1). As the acid catalyst to be used, there may be mentioned among others, sulfonic acids, such as p-toluenesulfonic acid and camphorsulfonic acid, sulfonic acid salts, such as pyridinium p-toluenesulfonate, and mineral acids, such as hydrochloric acid and sulfuric acid. Generally the amount of the acid catalyst is within the range of about 0.05 to 0.2 mole per mole of the aldehyde (VI-1). This reaction is generally carried out in a solvent. The amine or vinyl ether to be used may serve also as a solvent and it is possible to use a solvent, such as methylene chloride, tetrahydrofuran or dimethylformamide, which will not interfere with the reaction. Generally the amount of the solvent is within the range of about 5 to 200 parts per part of the aldehyde (VI-1) by weight. The reaction is generally carried out at a temperature within the range of about $-20°$ C. to $100°$ C., preferably within the range of about $0°$ C. to $30°$ C.

The aldehyde (VII-4) thus produced can be isolated and purified from the reaction mixture in the same manner as conventional isolation and purification procedures used in ordinary organic reactions. Thus, for example, the reaction mixture is poured into ice water, and the resulting mixture is extracted with an organic solvent, for example ether. When an organic base is used, the extract is washed with cold diluted hydrochloric acid. The extract is washed with an aqueous solution of sodium bicarbonate and an aqueous solution of sodium chloride, then dried and concentrated, and the resulting residue is purified by recrystallization of chromatography, for instance, to give the aldehyde (VII-4).

The aldehyde (VI-2) or aldehyde (VII) [including the aldehyde (VI-1)] is converted to the alcohol (I'-1) by reducing the aldehyde (VI-2) or aldehyde (VII). The reducing agent used in this reduction reaction is, for example, a metal hydride or a metal hydride complex, such as sodium borohydride, lithium borohydride, zinc borohydride, sodium triethylborohydride, lithium aluminum hydride, sodium bis(methoxyethoxy)aluminum hydride, diisobutylaluminum hydride, lithium tri-sec-butylborohydride or potassium tri-sec-butylborohydride. The amount of the reducing agent is within the range of about 0.25 to 50 moles, preferably about 0.5 to 20 moles per mole of the aldehyde (VI-2) or the aldehyde (VII). The reaction is generally carried out in a solvent. As the solvent to be used, which should be selected depending on the reducing agent employed, there may be mentioned, among others, ethanol, methanol, diethyl ether, tetrahydrofuran and dimethoxyethane. Generally the amount of the solvent is within the range of about 5 to 200 parts per part of the aldehyde (VI-2) or the aldehyde (VII) by weight. The reaction is generally carried out at a temperature within the range of about $-100°$ C. to 80° C., preferably within the range of about $-30°$ C. to 30° C. In case the aldehyde (VI-2) or aldehyde (VII) has an acyl or lower alkoxycarbonyl group as the hydroxy-protecting group and the reducing agent used is capable of reducing esters, for example lithium aluminium hydride, an alcohol of general formula (I'-1) in which $R^4$ and/or $R^5$ is a hydrogen atom is obtained as the product.

The alcohol (I'-1) thus produced can be isolated and purified from the reaction mixture in the same manner as conventional isolation and purification procedures used in ordinary organic reactions. Thus, for example, water, an aqueous solution of sodium sulfate, diluted hydrochloric acid or methanol is added to the reaction mixture with cooling in order to decompose the excess reducing agent and, after dilution with water as necessary, the resulting mixture is subjected to filtration, to extraction and washing, or to some other procedure to remove an organic solvent-insoluble substance. The organic layer thus obtained is concentrated and the resulting residue is purified by recrystallization or chromatography, for instance, to give the alcohol (I'-1).

The alcohol (I'-1) can be converted to the halide (I'-2-1) by any of those methods which are generally known for converting alcohols to the corresponding halides. Thus, for example, the alcohol (I'-1) is dissolved in about 5 to 200 parts per part of alcohol(I'-1) by weight, of an appropriate solvent, such as diethyl ether or pyridine, about 0.3 to 10 moles per mole of alcohol (I'-1), of a halogenating agent, such as phosphorus trichloride, phosphorus tribromide or thionyl chloride, is added to the solution at a temperature within the range of about $-20°$ C. to 10° C., and the mixture is stirred at a temperature within the above-mentioned range for about 15 minutes to about 12 hours. Alternatively, about 0.9 to 3 moles, per mole of alcohol (I'-1), of triphenylphosphine is admixed with about 0.9 mole to a solvent amount of a halogenating agent, such as carbon tetrachloride, carbon tetrabromide, bromine or iodine, in a solventless system or in about 5 to 200 parts per part of alcohol (I'-1) by weight, of a solvent, such as acetonitrile, dioxane, diethyl ether or methylene chloride, then the alcohol (I'-1) is added to the resulting reaction mixture, and the whole mixture is stirred at a temperature within the range of ambient temperature to about 100° C. for about 15 minutes to about 12 hours.

The halide (I'-2-1) thus produced can be isolated and purified from the reaction mixture in the same manner as conventional isolation and purification procedures used in ordinary organic reactions. Thus, for example, the reaction mixture is poured into ice water, the resulting mixture is extracted with an organic solvent, such as ether, the extract is washed in sequence with an aqueous solution of sodium bicarbonate and an aqueous solution of sodium chloride, then dried and concentrated, and the resulting residue is purified by recrystallization or chromatography, for instance, to give the halide (I'-2-1).

The alcohol (I'-1) can be converted to the sulfonate (I'-2-2) by any method generally known for converting alcohols to the corresponding sulfonates. Thus, for instance, it is treated with a sulfonyl chloride in the presence of a basic substance. The sulfonyl chloride to be used for the reaction is for example, an alkanesulfonyl chloride, such as methanesulfonyl chloride or ethanesulfonyl chloride, or an arenesulfonyl chloride, such as benzenesulfonyl chloride, p-toluenesulfonyl chloride, p-bromobenzenesulfonyl chloride or p-nitrobenzenesulfonyl chloride. The amount of the sulfonyl chloride is within the range of about 1.1 to 20 moles per mole of the alcohol (I'-1). The basic substance to be used in the reaction is, for example, an organic base, such as pyridine, triethylamine or diisopropylethylamine, a metal hydroxide, such as sodium hydroxide or potassium hydroxide, a metal hydride, such as sodium hydride, or an organometalic compound, such as n-butyl-lithium. The amount of the basic substance is within the range of about 1 to 1,000 moles per mole of the alcohol (I'-1). This reaction is generally carried out in a solvent. The organic base to be used as the basic substance may be used also as the solvent and it is possible to use a solvent, such as methylene chloride or chloroform, which will not interfere with the reaction. The amount of the solvent is within the range of about 5 to 200 parts per part of the alcohol (I'-1). The reaction is generally carried out at a temperature within the range of about $-20°$ C. to 30° C., preferably within the range of about 0° C. to 20° C.

The sulfonate (I'-2-2) thus produced can be isolated and purified from the reaction mixture in the same manner as is usual in conventional isolation and purification procedures used in ordinary organic reactions. Thus, for instance, the reaction mixture is poured into ice water, the resulting mixture is extracted with an organic solvent, for example diethyl ether, the extract is washed in sequence with cold diluted hydrochloric acid, an aqueous solution of sodium bicarbonate and an aqueous solution of sodium chloride, then dried and concentrated, and the resulting residue is purified by recrystallization or chromatography, for instance, to give the sulfonate (I'-2-2).

The alcohol (I'-1) can be converted to the sulfide (I'-2-3) by any conventional method known for converting alcohols to the corresponding sulfides. Thus, for example, the alcohol (I'-1) is converted to the halide (I'-2-1) and the latter is then treated with a thiol salt.

The thiol salt to be used can be prepared by treating the corresponding thiol with a basic substance. As the thiol to be used, there may be mentioned, among others, alkanethiols, such as methanethiol, ethanethiol, 2-propanethiol and 2-methyl-2-propanethiol, arenethiols, such as benzenethiol, toluenethiol, trimethylbenzenethiol, bromobenzenethiol, nitrobenzenethiol and methoxybenzenethiol, and heterocycle-substituted thiols, such as pyridinethiol. The amount of the thiol is within the range of about 0.8 to 50 moles per mole of the halide (I'-2-1). As the basic substance to be used, there may be mentioned, among others, metal hydroxides, such as sodium hydroxide and potassium hydroxide, metal alkoxides, such as sodium ethoxide and sodium methoxide, metal hydrides, such as sodium hydride, organometallic compounds, such as n-butyllithium, and organic bases, such as 1,8-diazabicyclo[5.4.0]undecene-7(DBU) and 1,5-diazabicyclo[4.3.0]nonene-5(DBN). The amount of the basic substance is within the range of about 0.1 to 10 moles per mole of the thiol. The reaction is generally carried in a solvent. Usable as the solvent are, for example, methanol, ethanol, dimethyl sulfoxide and dimethylformamide. The amount of the solvent is within the range of about 5 to 200 parts per part of the halide (I'-2-1) by weight. The reaction is generally carried out at a temperature within the range of about −10° C. to 150° C., preferably within the range of about 20° C. to 80° C.

The sulfide (I'-2-3) thus produced can be isolated and purified from the reaction mixture in the same manner as conventional isolation and purification procedures used in ordinary organic reactions. Thus, for example, the reaction mixture is concentrated as necessary, diluted with water and extracted with an organic solvent, for example diethyl ether, the extract is washed with an aqueous solution of sodium chloride, then dried and concentrated, and the resulting residue is purified by recrystallization or chromatography, for instance, to give the sulfide (I'-2-3).

The sulfoxide (I'-2-4) can be produced, for example by oxidizing the sulfide (I'-2-3) by a method generally known for converting sulfides to the corresponding sulfoxides. As the oxidizing agent to be used for the reaction, there may be mentioned, for example, sodium metaperiodate, peroxides, such as hydrogen peroxide and t-butyl hydroperoxide, and organic peracids, such as m-chloroperbenzoic acid and peracetic acid. The amount of the oxidizing agent is within the range of about 0.8 to 20 moles per mole of the sulfide (I'-2-3). The reaction is generally carried out in a solvent. Usable as the solvent are, for example, methanol, ethanol, water, acetic acid, methylene chloride, chloroform and other solvents which will not interfere with the reaction. The amount of the solvent is within the range of about 5 to 200 parts per part of the sufide (I'-2-3) by weight. The reaction is generally carried out at a temperature within the range of about −80° C. to 50° C., preferably within the range of about −20° C. to 30° C.

The sulfoxide (I'-2-4) thus produced can be isolated and purified from the reaction mixture in the same manner as conventional isolation and purification procedures used in ordinary organic reactions. Thus, for example, the reaction mixture is poured into water, the resulting mixture is extracted with an organic solvent, for example ethyl acetate, the extract is washed in sequence with an aqueous solution of sodium thiosulfate, an aqueous solution of sodium bicarbonate and an aqueous solution of sodium chloride, then dried and concentrated, and the resulting residue is purified by recrystallization or chromatography, for instance, to give the sulfoxide (I'-2-4).

The sulfone (I'-2-5) can be obtained in the conventional manner, for example by reacting the halide (I'-2-1) with a sulfinic acid salt or by oxidizing the sulfide (I'-2-3) or sulfoxide (I'-2-4). The sulfinic acid salt to be used is, for example, sodium benzenesulfinate or sodium toluenesulfinate. The amount of the sulfinic acid salt is within the range of about 0.8 to 50 moles per mole of the halide (I'-2-1). The reaction with a sulfinic acid salt is generally carried out in a solvent. As the solvent to be used, there may be mentioned methanol, ethanol, dimethylformamide and dimethyl sulfoxide, among others. Generally the amount of the solvent is within the range of about 5 to 200 parts per part of the halide (I'-2-1) by weight. The reaction with a sulfinic acid salt is generally carried out at a temperature within the range of about −20° C. to 150° C., preferably within the range of about 0° C. to 80° C. As the oxidizing agent to be used, there may be mentioned, among others, hydrogen peroxide, nitric acid, peracetic acid and m-chloroperbenzoic acid. Generally the amount of the oxidizing agent is within the range of about 0.5 to 20 moles per mole of the sulfide (I'-2-3) or sulfoxide (I'-2-4). The oxidation reaction is generally carried out in a solvent. Usable as the solvent are water, acetic acid, methanol, ethanol, methylene chloride, chloroform and other solvents which will not interfere with the reaction, The amount of the solvent is within the range of about 5 to 200 parts per part of the sulfide (I'-2-3) or the sulfoxide (I'-2-4) by weight. The oxidation reaction is generally carried out at a temperature within the range of about −30° C. to 120° C.

The sulfone (I'-2-5) thus produced can be isolated and purified from the reaction mixture in the same manner as conventional isolation and purification procedures used in ordinary organic reactions. Thus, for example, the reaction mixture is poured into ice water, the insoluble matter is collected by filtration, washed with water, and the resulting residue is purified by recrystallization or chromatography, for instance, to give the sulfone (I'-2-5).

It is also possible to convert the sulfonate (I'-2-2) to the halide (I'-2-1). For instance, the conversion reaction to halide (I'-2-1) can be carried out by stirring a mixture of the sulfonate (I'-2-2) and about 1.5 to 100 moles per mole of sulfonate (I'-2-2), of an alkali metal halide, such as sodium iodide, potassium iodide, sodium bromide, potassium bromide, lithium bromide or lithium chloride, in about 10 to 200 parts per part of sulfonate (I'-2-2) by weight, of an inert solvent, such as acetone or N,N-dimethylformamide, at a temperature within the range of ambient temperature to about 100° C. for about 15 minutes to 12 hours.

The halide (I'-2-1) thus produced can be isolated and purified from the reaction mixture in the same manner as conventional isolation and purification procedures used in ordinary organic reactions. Thus, for example, the reaction mixture is poured into water, the resulting mixture is extracted with ethyl acetate, methylene chloride, diethyl ether or the like solvent, the extract is washed in sequence with an aqueous solution of sodium thiosulfate, water, an aqueous solution of sodium bicarbonate and an aqueous solution of sodium chloride, then dried and concentrated, and the resulting residue is purified by recrystallization or chromatography, for instance, to give the halide (I'-2-1).

The aldehyde (VII) can be converted to the carboxylic acid (I''-1) by oxidizing the aldehyde (VII) by a general method of converting aldehydes to carboxylic acids. As the oxidizing agent to be used in this oxidation reaction, there may be mentioned, among others, chromium trioxide, potassium permanganate, silver oxide, potassium dichromate and pyridinium dichromate. The amount of the oxidizing agent is within the range of about 0.5 to 50 moles per mole of the aldehyde (VII). The reaction is generally carried out in a solvent. The solvent to be used includes, among others, water, ethanol, acetone and dimethylformamide, although it should be selected depending on the oxidizing agent employed. The amount of the solvent is within the range of about 5 to 200 parts per part of the aldehyde (VII) by weight. The reaction is generally carried out at a temperature within the range of about 0° C. to 80° C.

The carboxylic acid (I''-1) thus produced can be isolated and purified from the reaction mixture in the same manner as conventional isolation and purification procedures used in ordinary organic reactions. Thus, for example, isopropyl alcohol is added to the reaction mixture to decompose the excess oxidizing agent, the insoluble matter is filtered off, the filtrate is then concentrated under reduced pressure as necessary, diluted with water and extracted with an organic solvent, for example diethyl ether, the extract is washed with an aqueous solution of sodium chloride, then dried and concentrated, and the resulting residue is purified by recrystallization or chromatography, for instance, to give the carboxylic acid (I''-1).

The carboxylic acid (I''-1) can be converted to the ester (I''-2-1) by esterifying the carboxylic acid (I''-1) in the conventional manner. Thus, for example, the esterification can be carried out by treating the carboxylic acid (I''-1) with the corresponding alcohol or phenol to the desired ester (I''-2-1) in the presence of a condensing agent. Suited for used as the condensing agent are, for example, dicyclohexylcarbodiimide, 1-ethyl-3-(3-dimethylaminopropyl)carbodiimide hydrochloride, carbodiimidazole, N-ethyl-5-phenyl-isoxazolium-3'-sulfonic acid salt, 2-ethyl-7-oxybenzisoxazolium trifluoroboron salt and 1-ethoxycarbonyl-2-ethoxy-1,2-dihydroquinoline. The amount of the agent is within the range of about 0.8 to 20 moles per mole of carboxylic acid (I''-1). The reaction is generally carried out in a solvent. Usable as the solvent are diethyl ether, tetrahydrofuran, pyridine, methylene chloride, chloroform and other solvent which will not interfere with the reaction. The amount of the solvent is within the range of about 5 to 200 parts by weight per part by weight of carboxylic acid (I''-1). The reaction may be carried out in the presence of a catalytic amount of an activator such as 4-dimethylaminopyridine. The alcohol to be used includes, among others, alkanols, such as methanol, ethanol, 1-propanol, 2-propanol, 1-butanol, 2-methyl-1-propanol and 2-methyl-2-propanol, and benzyl alcohols, such as benzyl alcohol, nitrobenzyl alcohol, bromobenzyl alcohol and methoxybenzyl alcohol, while the phenol includes, among others, phenol, cresol, bromophenol and nitrophenol. The amount of the alcohol or the phenol is within the range of about 0.8 to 50 moles per mole of the carboxylic acid (I''-1). The reaction is generally carried out at a temperature within the range of about $-20°$ C. to 100° C., preferably within the range of about 0° C. to 50° C.

The ester (I''-2-1) thus produced can be isolated and purified from the reaction mixture in the same manner as conventional isolation and purification procedures used in ordinary organic reactions. Thus, for example, the reaction mixture is poured into water, the resulting mixture is extracted with an organic solvent, for example diethyl ether, the extract is washed in sequence with diluted hydrochloric acid, an aqueous solution of sodium bicarbonate and an aqueous solution of sodium chloride, then dried and concentrated, and the resulting residue is purified by recrystallization or chromatography, for instance, to give the ester (I''-2-1).

The methyl ester of general formula (I''-2) in which $R^3$ is a methyl group can be obtained also by treating the carboxylic acid (I''-1) with diazomethane. Thus, for instance, about 1 to 1.5 moles, per mole of carboxylic acid (I''-1), of diazomethane is blown into or an diethyl ether solution of said amount of diazomethane is gradually added to a solution or suspension of the carboxylic acid (I''-1) in about 5 to 200 parts per part of the carboxylic acid (I''-1) by weight, of an inert solvent, for example diethyl ether, tetrahydrofuran, methanol or methylene chloride, at a temperature within the range of about 0° C. to 40° C., to give the methyl ester of the carboxylic acid (I''-1).

The methyl ester of general formula (I''-2) in which $R^3$ is a methyl group can be isolated and purified from the reaction mixture by distilling off the unreacted diazomethane in a nitrogen stream or decomposing said unreacted diazomethane by addition of acetic acid, formic acid or the like and then proceeding in the same manner as conventional isolation and purification procedures used in ordinary organic reactions. Thus, for example, the reaction mixture obtained after distilling off or decomposing the unreacted diazomethane, after addition of an organic solvent, for example diethyl ether, as necessary, is washed in sequence with an aqueous solution of sodium bicarbonate and an aqueous solution of sodium chloride, then dried and concentrated, and the resulting residue is purified by recrystallization or chromatography, for instance, to give the desired methyl ester.

The carboxylic acid (I''-1) can be converted to the silyl ester (I''-2-2) by silylating the carboxylic acid (I''-1) in the conventional manner. Thus, for example, the silylation can be carried out by treating the carboxylic acid (I''-1) with a corresponding trisubstituted silyl chloride to desired silyl ester (I''-2-2) in the presence of a basic substance. As the trisubstituted silyl chloride to be used, there may be mentioned, among others, trialkylsilyl chlorides, such as trimethylsilyl chloride, triethylsilyl chloride, triisopropylsilyl chloride and t-butyldimethylsilyl chloride, and diarylalkylsilyl chlorides, such as t-butyldiphenylsilyl chloride. The amount of the trisubstituted silyl chloride is within the range of about 0.8 to 30 moles per mole of the carboxylic acid (I''-1). The basic substance to be used is, for example, pyridine, imidazole or triethylamine. The amount of the basic substance is within the range of about 2 to 1,000 moles per mole of carboxylic acid (I''-1). The reaction is generally carried out in a solvent. The basic substance to be used may serve also as a solvent and it is also possible to use a solvent, such as methylene chloride or dimethylformamide, which will not interfere with the reaction. The amount of the solvent is within the range of about 5 to 200 parts per part of the carboxylic acid (I''-1) by weight. The reaction is generally carried out at a temperature within the range of about $-20°$ C. to 80° C., preferably within the range of about 0° C. to 30° C.

The silyl ester (I''-2-2) thus produced can be isolated and purified from the reaction mixture in the same manner as conventional isolation and purification procedures used in ordinary organic reactions. Thus, for example, the reaction mixture is poured into water, the resulting mixture is extracted with an organic solvent, for example diethyl ether, the extract is washed with water and an aqueous solution of sodium chloride, then dried and concentrated, and the crude product thus obtained is purified by recrystallization or chromatography, for instance, to give the silyl ester (I''-2-2).

The carboxylic acid (I''-1), ester (I''-2-1) or silyl ester (I''-2-2) can be converted to the alcohol (I'-1) by reduction in the conventional manner. Usable as the reducing agent are, for example, lithium aluminum hydride and sodium bis(methoxyethoxy)aluminum hydride. The amount of the reducing agent is within the range of about 0.5 to 20 moles per mole of the carboxylic acid (I''-1), the ester (I''-2-1) or silyl ester (I''-2-2). The reaction is generally carried out in a solvent. Usable as the solvent are, for example, tetrahydrofuran, diethyl ether and 1,2-dimethoxyethane. The amount of the solvent is within the range of about 5 to 200 parts per part of the carboxylic acid (I''-1), the ester (I''-2-1) or the silyl ester (I''-2-2) by weight. The reaction is generally carried out at a temperature within the range of about $-80°$ C. to $70°$ C., preferably within the range of about $-10°$ C. to $30°$ C. When the carboxylic acid (I''-1), ester (I''-2-1) or silyl ester (I''-2-2) has an acyl or lower alkoxycarbonyl group as the hydroxyl-protecting group, the product is an alcohol (I'-1) in which $R^4$ and/or $R^5$ is a hydrogen atom.

The thus-produced alcohol (I'-1) can be isolated and purified from the reaction mixture in the same manner as conventional isolation and purification procedures used in ordinary organic reactions. Thus, for example, water, an aqueous solution of sodium sulfate, diluted hydrochloric acid, methanol or the like is added to the reaction mixture with cooling to decompose the excess reducing agent, the resulting mixture is diluted as necessary, the organic solvent-insoluble matter is removed by filtration, by extraction and washing or by some other appropriate means, the organic layer thus obtained is concentrated, and the resulting residue is purified by recrystallization or chromatography, for instance, to give the alcohol (I'-1).

The alcohol (I'-1) can be converted, as necessary, to the protected alcohol (I'-3) by protecting the hydroxyl group at position 21. The protected alcohol (I'-3) in turn can be converted, as necessary, to the alcohol (I'-1) by deprotecting the protected hydroxyl group at position 21.

The alcohol (I'-1) can be converted to the acyl ester (I'-3-1) by reacting the alcohol (I'-1) with a carboxylic acid anhydride or a carboxylic acid halide in the presence of a basic substance. Usable as the carboxylic acid anhydride to be used for this reaction, there may be mentioned, among others, acetic anhydride, propionic anhydride, butyric anhydride, monochloroacetic anhydride and trifluoroacetic anhydride. Usable as the carboxylic acid halide are, for example, acetyl chloride, propionyl chloride, butyryl chloride, isobutyryl chloride, valeryl chloride, isovaleryl chloride, pivaloyl chloride and benzoyl chloride. The amount of the carboxylic acid anhydride or the carboxylic acid halide is within the range of about 2 to 20 moles, preferably about 2.5 to 10 moles per mole of the alcohol (I'-1). As the basic substance to be used for this reaction, there may be mentioned, among others, organic bases, such as pyridine, triethylamine, diisopropylethylamine and diethylaniline, metal hydroxides, such as sodium hydroxide and potassium hydroxide, and metal hydrides, such as sodium hydride. Generally the amount of the basic substance is within the range of about 2 to 200 moles, preferably about 5 to 100 moles per mole of the alcohol (I'-1). This acylation reaction may be carried out in the presence of an acylation catalyst, such as dimethylaminopyridine or pyrrolidinopyridine. Generally the amount of the acylation catalyst is within the range of about 0.05 to 0.2 mole per mole of the alcohol (I'-1). This reaction is generally carried out in a solvent. The organic base employed may serve also as a solvent and it is also possible to use a solvent, such as methylene chloride or tetrahydrofuran, as an auxiliary solvent. Generally the amount of the solvent is within about 5 to 200 parts per part of the alcohol (I'-1) by weight. The reaction is generally carried out at a temperature within the range of about $-20°$ C. to $100°$ C., preferably within the range of about $0°$ C. to $30°$ C.

The acyl ester (I'-3-1) thus produced can be isolated and purified from the reaction mixture in the same manner as conventional isolation and purification procedures used in ordinary organic reactions. Thus, for example, the reaction mixture is poured into water, the resulting mixture is extracted with an organic solvent, for example ether, the extract is washed in sequence with cold diluted hydrochloric acid, an aqueous solution of sodium bicarbonate and an aqueous solution of sodium chloride, then dried and concentrated, and the resulting residue is purified by recrystallization or chromatography, for instance, to give the acyl ester (I'-3-1).

The acyl ester (I'-3-1) can be converted, if necessary, to the alcohol (I'-1) by deprotecting the protected hydroxyl group at position 21 in a conventional manner. The deprotection reaction can be carried out, for example by treating the acyl ester (I'-3-1) with water or a lower alcohol in the presence of a basic substance to thereby cause solvolysis. As the lower alcohol to be used, there may be mentioned, for example, methanol, ethanol and isopropyl alcohol. The amount of water or the lower alcohol is within the range of about 10 to 1,000 moles per mole of the acyl ester (I'-3-1). Usable as the basic substance are, for instance, metal carbonates, such as potassium carbonate and sodium carbonate, metal hydroxides, such as sodium hydroxide and potassium hydroxide, and metal alkoxides, such as sodium methoxide and sodium ethoxide. The amount of the basic substance is within the range of about 0.05 to 20 moles per mole of the acyl ester (I'-3-1). The reaction is generally carried out in a solvent. The reactant water or lower alcohol may be used also as a solvent and it is also possible to use a solvent such as tetrahydrofuran, methanol or ethanol, as an auxiliary solvent. The amount of the solvent is within the range of about 5 to 200 parts per part of the acyl ester (I'-3-1) by weight. The reaction is generally carried out at a temperature within the range of about $-20°$ C. to $100°$ C., preferably within the range of about $0°$ C. to $60°$ C.

The alcohol (I'-1) can be converted to the carbonate (I'-3-2) by treating the alcohol (I'-1) with a chlorocarbonate ester in the presence of a basic substance. The chlorocarbonate ester to be used for the reaction is, for example, methyl chlorocarbonate, ethyl chlorocarbonate and isopropyl chlorocarbonate. Generally the amount of the chlorocarbonate ester is within the range of about 2 to 50 moles, preferably about 5 to 20 moles per mole of the alcohol (I'-1). As the basic substance to be used in the reaction, there may be mentioned, among others, amines, such as pyridine, triethylamine, diisopropylethylamine and diethylaniline, metal hydroxides, such as sodium hydroxide and potassium hydroxide, and metal hydrides, such as sodium hydride. Generally the amount of the basic substance is within the range of about 2 to 200 moles, preferably about 5 to 100 moles per mole of the alcohol (I'-1). The reaction may be carried out in the presence of an esterification catalyst, such as dimethylaminopyridine or pyrrolidinopyridine. Generally the amount of the esterification catalyst is within the range of about 0.05 to 0.2 mole per mole of the alcohol (I'-1). This reaction is generally carried out in a solvent. The organic base employed may serve also as a solvent and it is also possible to use a solvent such as methylene chloride or tetrahydrofuran which will not interfere with the reaction, as an auxiliary solvent. Generally the amount of the solvent is within the range of about 5 to 200 parts per part of the alcohol (I'-1) by weight. The reaction is generally carried out at a temperature within the range of about −20° C. to 100° C., preferably within the range of about 0° C. to 30° C.

The carbonate (I'-3-2) can be isolated and purified from the reaction mixture in the same manner as conventional isolation and purification procedures used in ordinary organic reactions. Thus, for example, the reaction mixture is poured into ice water, the resulting mixture is extracted with an organic solvent, such as ether, the extract is washed in sequence with cold diluted hydrochloric acid, an aqueous solution of sodium bicarbonate and an aqueous solution of sodium chloride, then dried and concentrated, and the resulting residue is purified by recrystallization or chromatography, for instance, to give the carbonate (I'-3-2).

The carbonate (I'-3-2) can be converted, if necessary, to the alcohol (I'-1) by deprotecting the protected hydroxyl group at position 21. The deprotection reaction can be carried out, for example in the same manner as the above-mentioned conversion of acyl ester (I'-3-1) to alcohol (I -1), namely by solvolysis of the carbonate (I'-3-2) with water or a lower alcohol in the presence of a basic substance.

The alcohol (I'-1) can be converted to the silyl ether (I'-3-3) by treating the alcohol (I'-1) with a trisubstituted silyl chloride in the presence of a basic substance. The trisubstituted silyl chloride to be used for the reaction is, for example, a trialkylsilyl chloride, such as trimethylsilyl chloride, triethylsilyl chloride, triisopropylsilyl chloride or t-butyldimethylsilyl chloride, or a diarylalkylsilyl chloride, such as t-butyldiphenylsilyl chloride. Generally the amount of the trisubstituted silyl chloride is within the range of about 2 to 50 moles, preferably about 5 to 20 moles per mole of the alcohol (I'-1). As the basic substance to be used for the reaction, there may be mentioned, among others, amines, such as pyridine, triethylamine, diisopropylethylamine, diethylaniline and imidazole, metal hydroxides, such as sodium hydroxide and potassium hydroxide, and metal hydrides, such as sodium hydride. Generally the amount of the basic substance is within the range of about 2 to 200 moles, preferably 5 to 100 moles per mole of the alcohol (I'-1). This reaction is generally carried out in a solvent. The amine employed as the basic substance may be used also as the solvent and it is also possible to use a solvent such as methylene chloride, tetrahydrofuran or dimethylformamide which will not interfere with the reaction, as an auxiliary solvent. Generally the amount of the solvent is within the range of about 5 to 200 parts per part of the alcohol (I'-1) by weight. The reaction is generally carried out at a temperature within the range of about −20° C. to 100° C., preferably within the range of about 0° C. to 30° C.

The silyl ether (I'-3-3) can be isolated and purified from the reaction mixture in the same manner as conventional isolation and purification procedures used in ordinary organic reactions. Thus, for example, the reaction mixture is poured into ice water, the resulting mixture is extracted with an organic solvent, for example ether, the extract is washed in sequence with cold diluted hydrochloric acid, an aqueous solution of sodium bicarbonate and an aqueous solution of sodium chloride, then dried and concentrated, and the crude product thus obtained is purified by recrystallization or chromatography, for instance, to give the silyl ether (I'-3-3).

The silyl ether (I'-3-3) can be converted, if necessary, to the alcohol (I'-1) in the conventional manner by deprotecting the protected hydroxyl group at position 21. The deprotection reaction can be carried out for example by treating the silyl ether (I'-3-3) with water or a lower alcohol in the presence of fluoride ion. Usable as the lower alcohol are, for example, methanol, ethanol and isopropyl alcohol. The amount of water or the lower alcohol is within the range of about 10 to 1,000 moles per mole of silyl ether (I'-3-3). The fluoride ion source to be used is, for example, hydrofluoric acid or tetra-n-butylammonium fluoride and the amount of the fluoride ion source is within the range of about 1.1 to 50 moles per mole of the silyl ether (I'-3-3). The reaction is generally carried out in a solvent. Water or the lower alcohol may be used also as the solvent and it is also possible to use a solvent such as tetrahydrofuran, methanol or ethanol as an auxiliary solvent. Generally the amount of the solvent is within the range of about 5 to 200 parts per part of the silyl ether (I'-3-3) by weight. The reaction is generally carried out at a temperature within the range of about −20° C. to 100° C., preferably within the range of about 0° C. to 60° C.

The alcohol (I'-1) can be converted to the ether (I'-3-4) by treating the alcohol (I'-1) with a chloromethyl ether in the presence of a basic substance or by reacting the alcohol (I'-1) with a vinyl ether in the presence of an acid catalyst. The chloromethyl ether to be used is, for example, chloromethyl methyl ether or methoxyethoxymethyl chloride, and the vinyl ether is, for example, ethyl vinyl ether, methyl isopropenyl ether, dihydropyran or dihydrofuran. Generally the amount of the chloromethyl ether or the vinyl ether is within the range of about 2 to 50 moles, preferably about 5 to 20 moles per mole of the alcohol (I'-1). As the basic substance to be used for the reaction, there may be mentioned, among others, amines, such as pyridine, triethylamine, diisopropylethylamine, diethylaniline and imidazole, and metal hydrides, such as sodium hydride. Generally the amount of the basic substance is within the range of about 2 to 200 moles, preferably about 5 to 100 moles per mole of the alcohol (I'-1). Usable as the acid catalyst are, for example, sulfonic acids, such as p-toluenesulfonic acid and camphorsulfonic acid, sulfonic acid salts, such as pyridinium p-toluenesulfonate, and mineral acids, such as hydrochloric acid and sulfuric acid. Generally the amount of the acid catalyst is within the range of about 0.05 to 0.2 mole per mole of the alcohol (I'-1). This reaction is generally carried out in a solvent. The amine or vinyl ether to be used may serve also as a solvent. It is also possible to use a solvent such as methylene chloride, tetrahydrofuran or dimethylformamide which will not interfere with the reaction, as an auxiliary solvent. Generally the amount of the solvent is within the range of about 5 to 200 parts per part of the alcohol (I'-1) by weight. The reaction is generally carried out at a temperature within the range of about −20° C. to 100° C., preferably within the range of about 0° C. to 30° C.

The ether (I'-3-4) can be isolated and purified from the reaction mixture in the same manner as conventional isolation and purification procedures used in ordinary organic reactions. Thus, for example, the reaction mixture is poured into ice water, the resulting mixture is extracted with an organic solvent, for example ether, the extract, after washing with cold diluted hydrochloric acid in case an amine has been used in the reaction, is washed in sequence with an aqueous solution of sodium bicarbonate and an aqueous solution of sodium chloride, then dried and concentrated, and the resulting residue is purified by recrystallization or chromatography, for instance, to give the ether (I'-3-4).

The ether (I'-3-4) can be converted, if necessary, to the alcohol (I'-1) in the conventional manner by deprotecting the protected hydroxyl group at position 21. For example, the deprotection reaction can be carried out by treating the ether (I'-3-4) with water or a lower alcohol in the presence of an acid catalyst. Usable as the lower alcohol are methanol, ethanol and isopropyl alcohol, among others. The amount of the water or the lower alcohol is within the range of about 10 to 1,000 moles per mole of the ether (I'-3-4). As the acid catalyst to be used, there may be mentioned p-toluenesulfonic acid, acetic acid, hydrochloric acid, sulfuric acid, pyridinium p-toluene-sulfonate, and the like. The amount of the acid catalyst is within the range of about 0.02 to 10 moles per mole of the ether (I'-3-4). Water and the lower alcohol may be used also as the solvent and it is further possible to use a solvent such as tetrahydrofuran, methanol or ethanol, as an auxiliary solvent. Generally the amount of the solvent is within the range of about 5 to 200 parts per part of the ether (I'-3-4) by weight. The reaction is generally carried out at a temperature within the range of about −20° C. to 100° C., preferably within the range of about 0° C. to 60° C.

The cholesta-5,7-diene derivatives of general formula (II) and the 9,10-secocholesta-5,7,10(19)-triene derivatives of general formula (III) can be produced from the sulfone (I'-2-5) by the processes shown below:

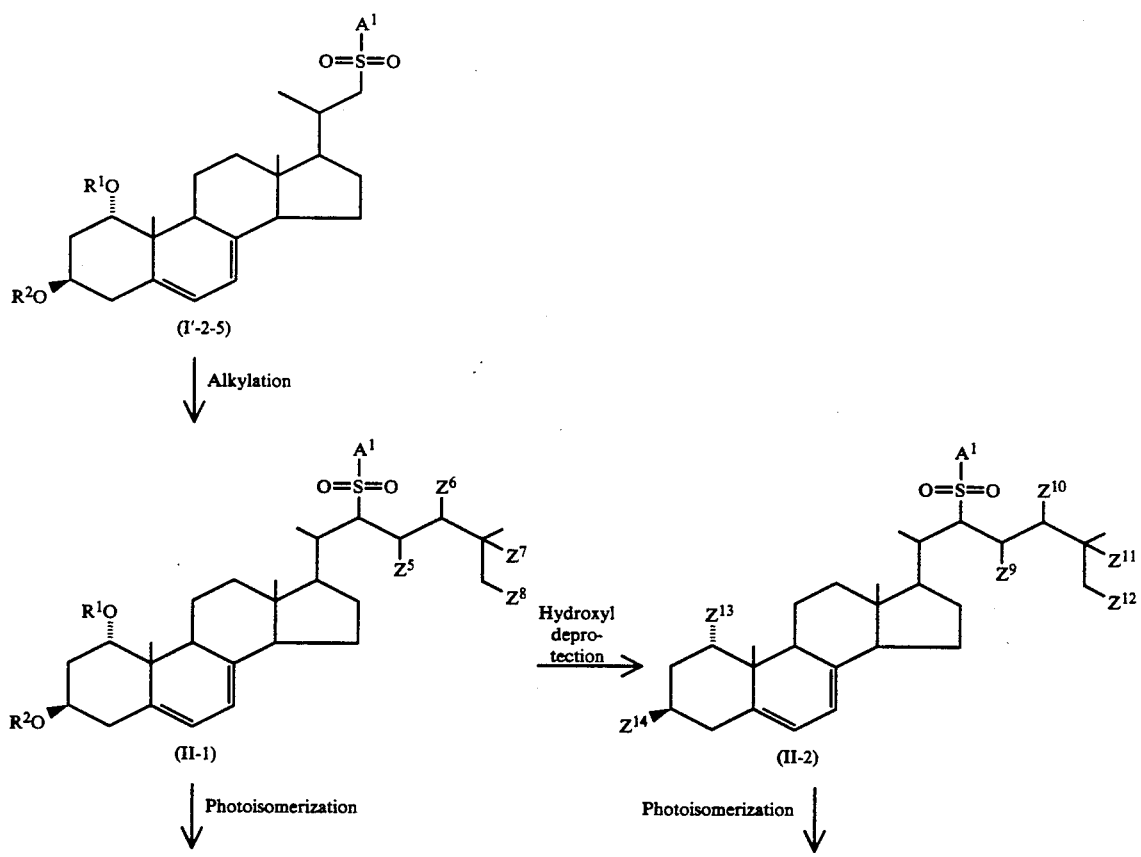

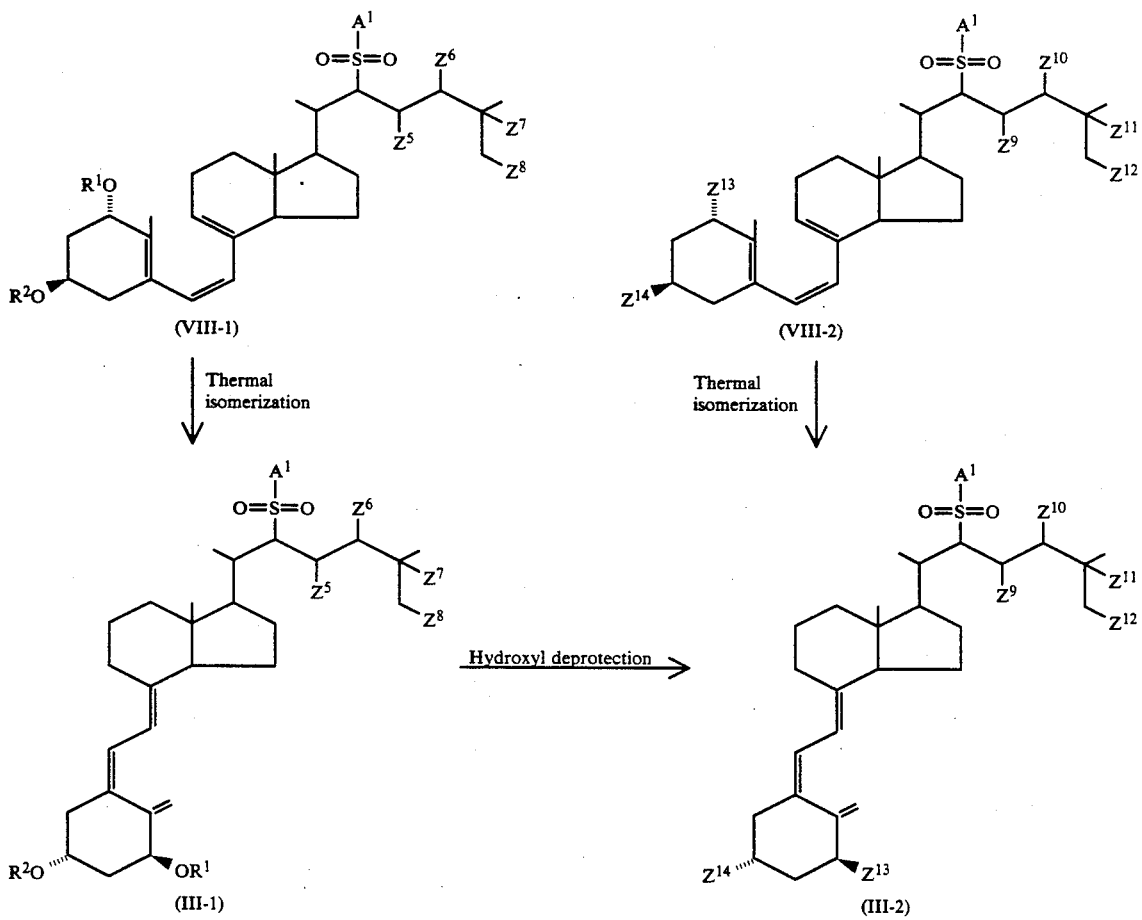

In the above formulas $R^1$, $R^2$ and $A^1$ are as defined above, $Z^5$, $Z^6$, $Z^7$ and $Z^8$ each is a hydrogen atom, a hydroxyl group or a protected hydroxyl group, $Z^9$, $Z^{10}$, $Z^{11}$ and $Z^{12}$ each is a hydrogen atom, a hydroxyl group or a protected hydroxyl group, and $Z^{13}$ and $Z^{14}$ each is a hydroxyl group or a protected hydroxyl group provided that at least one of $Z^9$, $Z^{10}$, $Z^{11}$, $Z^{12}$, $Z^{13}$ and $Z^{14}$ is a hydroxyl group.

Referring to the above formulas, the compounds represented by the general formula (II-1) or (II-2) are included in the class of cholesta-5,7-diene derivatives of general formula (II) and the compounds represented by the general formula (III-1) or (III-2) are included in the class of 9,10-secocholesta-5,7,10(19)-triene derivatives of general formula (III).

The compounds represented by the above general formulas (II-1), (II-2), (III-1), (III-2), (VIII-1) and (VIII-2) are hereinafter sometimes referred to, respectively, as follows:

| General formula | To be referred to as: |
|---|---|
| (II-1) | Cholesta-5,7-diene derivative (II-1) |
| (II-2) | Cholesta-5,7-diene derivative (II-2) |
| (III-1) | 9,10-Secocholesta-5,7,10(19)-triene derivative (III-1) |
| (III-2) | 9,10-Secocholesta-5,7,10(19)-triene derivative (III-2) |
| (VIII-1) | 9,10-Secocholesta-5(10),6,8-triene derivative (VIII-1) |
| (VIII-2) | 9,10-Secocholesta-5(10),6,8-triene derivative (VIII-2) |

The sulfone (I'-2-5) is first converted to the cholesta-5,7-diene derivative (II-1) by treating the sulfone (I'-2-5) with an alkylating agent in the presence of a basic substance. The basic substance which should be capable of metallizing the sulfone (I'-2-5) at the α-position to the substituted sulfonyl group (namely the position 21) includes, among others, organometallic compounds, such as n-butyllithium, sec-butyllithium, tert-butyllithium, methyllithium and phenyllithium, and metal amides, such as lithium amide, sodium amide, lithium diisopropylamide, lithium hexamethyldisilazide, sodium hexamethyldisilazide and lithium tetramethylpiperazide. The alkylating agent to be used is, for example, a compound of the general formula

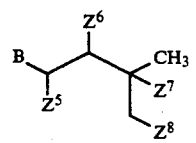

(IX-1)

wherein $Z^5$, $Z^6$, $Z^7$ and $Z^8$ are as defined above and B is a halogen atom or a group of the formula

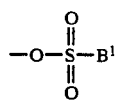

in which $B^1$ is a lower alkyl group, an aryl group or an aralkyl group [hereinafter sometimes referred to as "alkylating agent (IX-1)"], an epoxide of the general formula

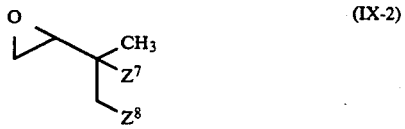

(IX-2)

wherein $Z^7$ and $Z^8$ are as defined above [hereinafter sometimes referred to as "alkylating agent (IX-2)], or an aldehyde of the general formula

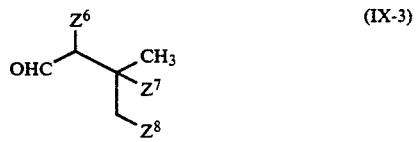

(IX-3)

wherein $Z^6$, $Z^7$ and $Z^8$ are as defined above [hereinafter sometimes referred to as "alkylating agent (IX-3)"]. Referring to the group $B^1$ which the alkylating agent (IX-1) may have, the lower alkyl group is, for example, methyl, ethyl or isopropyl, the aryl group is, for example, phenyl, p-tolyl or p-bromophenyl, and the aralkyl group is, for example, benzyl or p-methoxybenzyl. When the alkylating agent (IX-2) is used as the alkylating agent, the product is a cholesta-5,7-diene derivative of general formula (II-1) in which $Z^5$ is a hydrogen atom and $Z^6$ is a hydroxyl group. When the alkylating agent (IX-3) is used as the alkylating agent, a cholesta-5,7-diene derivative of general formula (II-1) in which $Z^5$ is a hydroxyl group is obtained. Generally the amount of the basic substance is within the range of about 0.5 to 10 moles, preferably about 0.8 to 5 moles per mole of the sulfone (I'-2-5). Generally the amount of the alkylating agent is within the range of about 0.5 to 10 moles, preferably about 0.8 to 5 moles per mole of the sulfone (I'-2-5). The reaction is generally carried out in a solvent. Usable as the solvent are those which will not interfere with the reaction, for example diethyl ether, dimethoxyethane and tetrahydrofuran. Generally the amount of the solvent is within the range of about 5 to 200 parts per part of the sulfone (I'-2-5) by weight. The reaction may carried out in the presence of an amount of about 0.5 to 5 moles per mole of the sulfone (I'-2-5), of hexamethylphosphoric triamide, tetramethylethylenediamine, triethylenediamine or the like. The reaction is generally carried out at a temperature within the range of about −100° C. to 20° C. for a period of about 15 minutes to 24 hours, although the reaction period should be varied depending on the reaction temperature employed. It is simple and easy to carry the reaction out by mixing and treating the sulfone (I'-2-5) or a solution of the sulfone (I'-2-5) with the basic substance at a temperature within the above-mentioned range, and then adding the alkylating agent or a solution of the alkylating agent to the mixture prepared above, and stirring the resulting mixture at a temperature within the above-mentioned range.

The cholesta-5,7-diene derivative (II-1) can be isolated and purified from the reaction mixture in the same manner as conventional isolation and purification procedures used in ordinary organic reactions. Thus, for example, the reaction mixture is poured into an aqueous saturated solution of ammonium chloride, the resulting mixture is extracted with an organic solvent, for example diethyl ether, the extract is washed in sequence with an aqueous solution of sodium bicarbonate and an aqueous solution of sodium chloride, then dried and concentrated, and the resulting residue is purified by recrystallization or chromatography, for instance, to give the cholesta-5,7-diene derivative (II-1).

The cholesta-5,7-diene derivative (II-1) can be converted, if necessary, to the cholesta-5,7-diene derivative (II-2) by deprotecting the protected hydroxyl group or groups in a conventional manner. When the hydroxyl-protecting group is an acyl group, the deprotection reaction can be carried out in the same manner as mentioned above for the deprotection reaction to be employed in converting the acyl ester (I'-3-1) to the alcohol (I'-1). When the hydroxyl-protecting group is a lower alkoxycarbonyl group or carbonyl group, this protected hydroxyl group can be deprotected in the same manner as mentioned above for the deprotection reaction to be employed for the conversion of the carbonate (I'-3-2) to the alcohol (I'-1). When the hydroxyl-protecting group is a trisubstituted silyl group, this protected hydroxyl group can be deprotected in the same manner as mentioned above for the deprotection reaction to be used in converting the silyl ether (I'-3-3) to the alcohol (I'-1). Similarly, when the hydroxyl-protecting group is an alkoxymethyl group which may optionally be substituted, this protected hydroxyl group can be deprotected in the same manner as mentioned above for the deprotection reaction to be employed in converting the ether (I'-3-4) to the alcohol (I'-1).

The cholesta-5,7-diene derivative (II-1) or (II-2) can be converted to the 9,10-secocholesta-5(10),6,8-triene derivative (VIII-1) or (VIII-2) by irradiating the cholesta-5,7-diene derivative (II-1) or (II-2) with ultraviolet light. Generally, the wavelength of the ultraviolet light is within the range of about 200 to 360 nm, preferably about 260 to 310 nm. This photoisomerization reaction is generally carried out in a solvent. Usable as the solvent are, for example, hydrocarbon solvents, such as hexane, heptane, cyclohexane, ligroin, benzene, toluene and xylene, halogenated hydrocarbon solvents, such as bromobenzene, chlorobenzene, carbon tetrachloride, 1,2-dichloroethane and 1,2-dibromoethane, ether solvents, such as diethyl ether, tetrahydrofuran, dioxane and ethyl cellosolve, and alcohol solvents, such as methanol, ethanol and propanol. The reaction is carried at a temperature within the range of about −20° C. to 120° C., preferably within the range of about −10° C. to 20° C.

The 9,10-secocholesta-5(10),6,8-triene derivative (VIII-1) or (VIII-2) can be isolated and purified from the reaction mixture in the same manner as conventional isolation and purification procedures used in ordinary organic reactions. Thus, for example, the reaction mixture is concentrated under reduced pressure and the resulting residue is purified by recrystallization or chromatography, for instance, to give the 9,10-secocholesta-5(10),6,8-triene derivative (VIII-1) or (VIII-2) as a purified product. It is also possible to use in the next step the crude 9,10-secocholesta-5(10),6,8-triene derivative (VIII-1) or (VIII-2) without purification to be converted to the 9,10-secocholesta-5,7,10(19)-triene derivative.

The 9,10-secocholesta-5(10),6,8-triene derivative (VIII-1) or (VIII-2) can be converted to the 9,10-secocholesta-5,7,10(19)-triene derivative (III-1) or (III-2) by isomerizing the 9,10-secocholesta-5(10),6,8-triene derivative (VIII-1) or (VIII-2) with thermal energy. This thermal isomerization reaction is generally carried out at a temperature within the range of about 20° C. to 120° C., preferably within the range of about 40° C. to 100° C. The reaction is generally carried out in a solvent. As the solvent to be used, there may be mentioned those usable in the above-mentioned ultraviolet irradiation, for instance.

The 9,10-secocholesta-5,7,10(19)-triene derivative (III-1) or (III-2) can be isolated and purified from the reaction mixture in the same manner as conventional isolation and purification procedures used in ordinary organic reactions. Thus, for example, the reaction mixture is concentrated under reduced pressure and the resulting residue is purified by recrystallization or chromatography, for instance, to give the 9,10-secocholesta-5,7,10(19)-triene derivative (III-1) or (III-2).

Furthermore, as mentioned above, the 9,10-secocholesta-5(10),6,8-triene derivative (VIII-1) or (VIII-2) to be converted to the 9,10-secocholesta-5,7,10(19)-triene derivative (III-1) or (III-2) need not be isolated in a purified form. Therefore, the 9,10-secocholesta-5,7,10(19)-triene derivative (III-1) or (III-2) can be obtained also by irradiating the cholesta-5,7-diene derivative (II-1) or (II-2) with ultraviolet light in the manner mentioned above, followed by isomerizing the irradiation product with thermal energy.

The 9,10-secocholesta-5,7,10(19)-triene derivative (III-1) can be converted, if necessary, to the 9,10-secocholesta-5,7,10(19)-triene derivative (III-2) by deprotecting the protected hydroxyl group or groups in a conventional manner. This deprotection reaction can be carried out by an appropriate method selected depending on the kind of hydroxyl-protecting group, for example from among the methods mentioned above as usable in converting the cholesta-5,7-diene derivative (II-1) to the cholesta-5,7-diene derivative (II-2).

The 9,10-secocholesta-5,7,10(19)-triene derivative of general formula (III) can be converted to a vitamin $D_3$ derivative of general formula (X) which has a hydroxyl group at the 1α-position, for example by the process shown below:

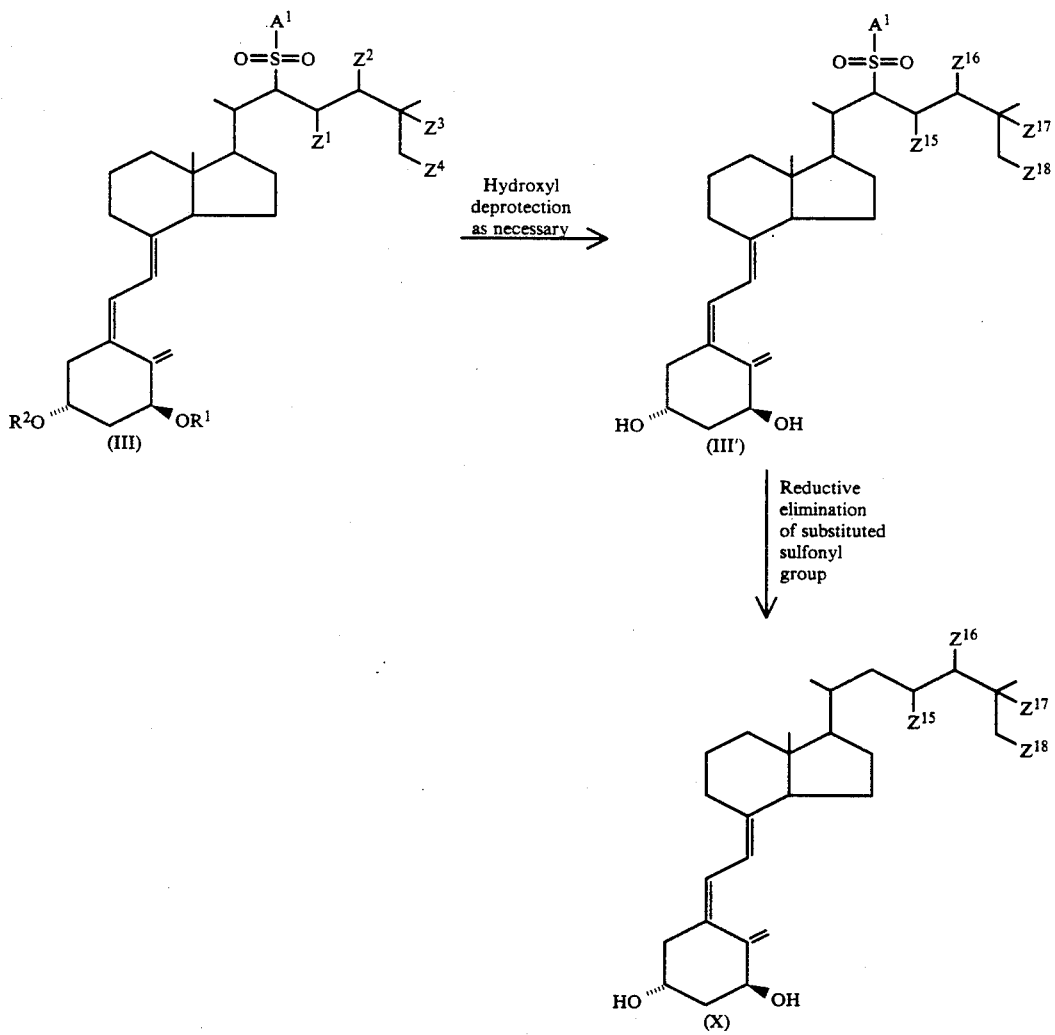

In the above formulas, $R^1$, $R^2$, $A^1$, $Z^1$, $Z^2$, $Z^3$ and $Z^4$ are as defined above and $Z^{15}$, $Z^{16}$, $Z^{17}$ and $Z^{18}$ each is a hydrogen atom or a hydroxyl group.

Thus, the 9,10-secocholesta-5,7,10(19)-triene derivative of general formula (III) is subjected, if necessary, to hydroxyl deprotection in the same manner as mentioned above to convert all the protected hydroxyl groups to free hydroxyl groups and then the substituted sulfonyl group at position 21 of the 9,10-secocholesta-5,7,10(19)-triene derivative of general formula (III') is eliminated by a conventional method known for reductive elimination of substituted sulfonyl groups, for example by reductive treatment with a reducing agent such as sodium amalgam, whereby a vitamin D3 derivative of general formula (X) which has a hydroxyl group at the 1α-position can be obtained.

BEST MODE FOR CARRYING OUT THE INVENTION

The following examples are further illustrative of this invention. It should, of course, be understood that this invention is by no means limited to the specific examples disclosed.

REFERENCE EXAMPLE 1

In 100 ml of methylene chloride containing 1% of pyridine was dissolved 2.74 g of 1α,3β-diacetoxy-5α,8α-(3,5-dioxo-4-phenyl-1,2,4-triazolidino) cholesta-6,22-dien-24-ol and the solution was stirred in a dry ice-acetone bath. To the solution was added 425 ml of a saturated solution of ozone in methylene chloride containing 1% of pyridine which was prepared by ozone gas bubbling into the solvent in a dry ice-acetone bath. After it was confirmed that the blue color of ozone had disappeared, 5 ml of dimethyl sulfide was added and the cooling bath was removed to allow the reaction mixture to warm to ambient temperature. The reaction mixture was sequentially washed with cold 2% hydrochloric acid and water, dried over sodium sulfate and concentrated. The residue was purified by silica gel column chromatography to give 880 mg of 1α,3β-diacetoxy-5α,8α-(3,5-dioxo-4-phenyl-1,2,4 -triazo-lidino)-6-pregnene-20-carbaldehyde.

$^1$H NMR spectrum (90 MHz) $\delta_{TMS}$CDCl$_3$: 0.87 (s, 3H), 1.01 (s, 3H), 1.17 (d, J=7 Hz, 3H), 1.97 & 1.98 (each s, 6H), 5.03 (m, 1H), 5.84 (m, 1H), 6.28, 6.41 (ABq, J=8 Hz, 2H), 7.2–7.6 (m, 5H), 9.58 (d, J=4 Hz, 1H).

REFERENCE EXAMPLE 2

To 302 mg of 1α,3β-diacetoxy-5α,8α-(3,5-dioxo-4-phenyl-1,2,4-triazolidino)-6 -pregnene-20-carbaldehyde was added 5 ml of 2.1 N-potassium hydroxide in 95% ethanol and the mixture was refluxed under argon atmosphere for 1.5 hours. After cooling, the reaction mixture was poured into water and extracted with diethyl ether. The extract was washed with aqueous sodium chloride solution, dried over sodium sulfate and concentrated. The residue was purified by recrystallization from diethyl ether to give 163 mg of 1α,3β-dihydroxypregna-5,7-diene-20-carbaldehyde.

$^1$H NMR spectrum (90 MHz) $\delta_{TMS}$CDCl$_3$: 0.71 (s, 3H), 0.92 (s, 3H), 1.06 (d, J=7 Hz, 3H), 3.2–3.8 (m, 1H), 4.0–4.3 (m, 1H), 5.3–5.5 (m, 1H), 5.6–5.8 (m, 1H), 9.54 (d, 1H).

REFERENCE EXAMPLE 3

To 181 mg of 1α,3β-diacetoxy-5α,8α-(3,5-dioxo-4-phenyl-1,24-triazolidino)-6-pregnene -20-carbaldehyde was added 30 ml of collidine and the mixture was refluxed under argon atmosphere for 15 minutes. After cooling, the reaction mixture was extracted with ethyl acetate and the extract was washed serially with 1N-HCl, aqueous sodium hydrogen carbonate solution and aqueous sodium chloride solution, dried over medium sulfate and concentrated. The residue was purified by silica gel column chromatography to give 73 mg of 1α,3β-diacetoxypregna-5,7-diene-20-carbaldehyde.

$^1$H NMR spectrum (90 MHz) $\delta_{TMS}$CDCl$_3$: 0.66 (s, 3H), 1.02 (s, 3H), 1.15 (d, J=6.4 Hz, 3H), 2.00 & 2.05 (each s, 6H), 4.6–5.2 (2H), 5.40 (m, 1H), 5.65 (m, 1H), 9.58 (d, J=3.5 Hz, 1H).

REFERENCE EXAMPLE 4

IN 2 ml of methanol was dissolved 73 mg of 1α,3β-diacetoxypregna-5,7-diene-20-carbaldehyde, followed by addition of 5 mg of potassium carbonate. The mixture was stirred at room temperature for 12 hours. The reaction mixture was poured into water and extracted with diethyl ether, and the extract was washed with aqueous sodium chloride solution, dried over sodium sulfate and concentrated. The residue was recrystallized from ether to give 49 mg of 1α,3β-dihydroxypregna-5,7-diene-20-carbaldehyde which showed the same $^1$H NMR spectrum as the 1α,3β-dihydroxypregna-5,7-diene-20-carbaldehyde obtained in Reference Example 2.

REFERENCE EXAMPLE 5

In 1 ml of methylene chloride was suspended 69 mg of 1α,3β-dihydroxypregna-5,7-diene-20-carbaldehyde, followed by addition of 0.3 ml of pyridine, and the mixture was stirred with ice-cooling. Then, 5 mg of dimethylaminopyridine was added and 0.15 ml of methyl chlorocarbonate was further added dropwise. After completion of the addition, the reaction mixture was stirred at ambient temperature for 10 hours. This reaction mixture was poured into ice-water and extracted with diethyl ether. The extract was serially washed with cold 1N-HCl, aqueous sodium hydrogen carbonate solution and aqueous sodium chloride solution, dried over sodium sulfate and concentrated. The residue was purified by silica gel column chromatography to give 61 mg of 1α,3β-bis(methoxycarbonyloxy)-pregna-5,7-diene-20-carbaldehyde.

$^1$H NMR spectrum (90 MHz) $\delta_{TMS}$CDCl$_3$: 0.66 (s, 3H), 1.02 (s, 3H), 1.15 (d, J=6.4 Hz, 3H), 3.77 & 3.79 (each s, 6H), 4.6–5.2 (2H), 5.40 (m, 1H), 5.65 (m, 1H), 9.58 (d, J=3.5 Hz, 1H).

REFERENCE EXAMPLE 6

In 1 ml of N,N-dimethylformamide was dissolved 69 mg of 1α,3β-dihydroxypregna-5,7-diene-20-carbaldehyde, followed by addition of 0.2 g of imidazole and 0.2 g of t-butyldimethylsilyl chloride in that order. The mixture was stirred at room temperature for 20 hours. The reaction mixture was then poured into water and extracted with diethyl ether. The extract was washed with aqueous sodium chloride solution, dried over sodium sulfate and concentrated. The residue was purified by silica gel column chromatography to give 75 mg of 1α,3β-bis(t-butyldimethylsilyloxy)pregna-5,7-diene-20-carbaldehyde.

$^1$H NMR spectrum (90 MHz) $\delta_{TMS}$CDCl$_3$: 0.11 & 0.13 (each s, 12H), 0.70 (s, 3H), 0.88 (s, 3H), 0.95 & 0.96 (each s, 18H), 1.15 (d, J=6.4 Hz, 3H), 4.1–4.5 (2H), 5.39 (m, 1H), 5.64 (m, 1H), 9.55 (d, J=3.5 Hz, 1H).

REFERENCE EXAMPLE 7

In 0.5 ml of N,N-diisopropylethylamine was dissolved 69 mg of 1α,3β-dihydroxypregna-5,7-diene-20-carbaldehyde, followed by addition of 20 mg of chloromethyl methyl ether. The mixture was stirred at room temperature for 24 hours. The reaction mixture was then poured into cold diluted hydrochloric acid and extracted with diethyl ether. The extract was serially washed with aqueous sodium hydrogen carbonate solution and aqueous sodium chloride solution, dried over sodium sulfate and concentrated. The residue was purified by silica gel column chromatography to give 70 mg of 1α,3β-bis(methoxymethoxy)pregna-5,7-diene-20-carbaldehyde.

$^1$H NMR spectrum (90 MHz) $\delta_{TMS}$CDCl$_3$: 0.66 (s, 3H), 0.92 (s, 3H), 1.14 (d, J=6 Hz, 3H), 3.30 & 3.34 (each s, 6H), 4.0–4.4 (2H), 4.75–4.85 (4H), 5.38 (m, 1H), 5.64 (m, 1H), 9.56 (d, J=3.5 Hz, 1H).

EXAMPLE 1

In 2 ml of ethanol was dissolved 100 mg of 1α,3β-bis(methoxycarbonyloxy)pregna-5,7-diene-20-carbaldehyde. Then, under ice-cooling, 20 mg of sodium borohydride was added and the reaction mixture was stirred for 30 minutes. The reaction mixture was neutralized with diluted hydrochloric acid under ice-cooling and, after diluted with water, extracted with diethyl ether. The extract was serially washed with aqueous sodium hydrogen carbonate solution and aqueous sodium chloride solution, dried over sodium sulfate and concentrated under reduced pressure. The residue was purified by silica gel column chromatography to give 83 mg of 20-methyl-1α,3β-bis)methoxycarbonyloxy)pregna-5,7-dien-21-ol.

$^1$H NMR spectrum (90MHz) $\delta_{TMS}$CDCl$_3$: 0.73 (s, 3H), 1.00 (s, 3H), 1.01 (d, J=7 Hz, 3H), 3.50 (m, 2H), 3.77 (s, 3H), 3.79 (s, 3H), 4.6–5.2 (2H), 5.40 (m, 1H), 5.65 (m, 1H).

EXAMPLE 2

IN 1 ml of pyridine was dissolved 75 mg of 20-methyl-1α,3β-bis(methoxycarbonyloxy)pregna-5,7-dien-21-ol and, then, under ice-cooling, 0.05 ml of phosphorus tribromide was added. The mixture was stirred at the same temperature for 15 minutes. The reaction mixture was then poured into ice water and extracted with diethyl ether. The extract was washed with aqueous sodium hydrogen carbonate solution and aqueous sodium chloride solution, dried over anhydrous sodium sulfate and concentrated. The residue was purified by silica gel column chromatography to give 53 mg of 21-bromo-20-methyl-1α,3β-bis(methoxycarbonyloxy)pregna-5,7-diene.

$^1$H NMR spectrum (90 MHz) $\delta_{TMS}$CDCl$_3$: 0.75 (s, 3H), 1.01 (s, 3H), 1.01 (d, J=7 Hz, 3H), 3.41 (m, 2H), 3.78 (s, 3H), 3.79 (s, 3H), 4.6–5.2 (2H), 5.39 (m, 1H), 5.64 (m, 1H).

EXAMPLE 3

In 1 ml of pyridine was dissolved 81 mg of 20-methyl-1α,3β-bis(methoxycarbonyloxy)pregna-5,7-dien-21 -ol and, then, under ice-cooling, 70 mg of p-toluenesulfonyl chloride was added. The mixture was stirred at that temperature for 3 hours. The reaction mixture was then poured into ice water and extracted with diethyl ether. The extract was serially washed with aqueous copper sulfate solution, water, aqueous sodium hydrogen carbonate solution and aqueous sodium chloride solution, dried over anhydrous sodium sulfate and concentrated. The residue was purified by silica gel column chromatography to give 79 mg of 20-methyl-1α,3β-bis(methoxycarbonyloxy)-21-p-toluenesulfonyloxypregna-5,7-diene.

$^1$H NMR spectrum (90 MHz) $\delta_{TMS}$CDCl$_3$: 0.62 (s, 3H), 0.93 (d, J=7 Hz, 3H), 0.95 (s, 3H), 2.38 (s, 3H), 3.77 (s, 3H), 3.79 (s, 3H), 3.85 (m, 2H), 4.6–5.2 (2H), 5.40 (m, 1H), 5.59 (m, 1H), 7.36 (d, J=8 Hz, 2H), 7.82 (d, J=8 Hz, 2H).

EXAMPLE 4

In 2 ml of dimethyl sulfoxide under ice-cooling, 55 mg of thiophenol and 20 mg of sodium hydroxide were stirred. Then, 54 mg of 21-bromo-20-methyl-1α,3β-bis(methoxycarbonyloxy)pregna-5,7-diene was added and the mixture was further stirred at ambient temperature for 3 hours. The reaction mixture was then poured into water and extracted with diethyl ether. The extract was washed with water and aqueous sodium chloride solution, dried over anhydrous sodium sulfate and concentrated. The residue was purified by silica gel column chromatography to give 39 mg of 20-methyl-1α,3β-bis(methoxycarbonyloxy)-21-phenylthiopregna-5, 7-diene.

$^1$H NMR spectrum (90 MHz) $\delta_{TMS}$CDCl$_3$: 0.65 (s, 3H), 0.95 (d, J=7 Hz, 3H), 1.00 (s, 3H), 2.84 (m, 2H), 3.76 (s, 3H), 3.79 (s, 3H), 4.6–5.2 (2H), 5.38 (m, 1H), 5.64 (m, 1H), 7.22 (5H).

EXAMPLE 5

To 3 ml of dimethylformamide were added 65 mg of 21-bromo-20-methyl-160 ,3β-bis(methoxycarbonyloxy)pregna-5,7-diene and 80 mg of sodium benzenesulfinate and the mixture was stirred at 75° C. for 5 hours. After cooling, the reaction mixture was poured into water and extracted with methylene chloride. The extract was washed with water and aqueous sodium chloride solution, dried over sodium sulfate and concentrated. The residue was purified by silica gel column chromatography to give 49 mg of 20-methyl-1α,3β-bis(methoxycarbonyloxy)-21-phenylsulfonylpregna-5,7-diene.

$^1$H NMR spectrum (90 MHz) $\delta_{TMS}$CDCl$_3$: 0.71 (s, 3H), 1.01 (d, J=7 Hz, 3H), 1.02 (s, 3H), 3.10 (m, 2H), 3.77 (s, 3H), 3.39 (s, 3H), 4.6–5.3 (2H), 5.40 (m, 1H), 5.65 (m, 1H), 7.4–8.1 (5H).

EXAMPLE 6

In 5 ml of acetone was dissolved 120 mg of 1α,3β-bis(methoxycarbonyloxy)pregna-5,7-diene-20-carbaldehyde and the solution was stirred with ice-cooling. Then, Jones' reagent prepared by mixing chromic acid with concentrated sulfuric acid and diluting the mixture with water in accordance with the method of K. Bowden et al. (J. Chem. Soc., p. 39, (1946)) was added dropwise to the above solution until the red color of the reagent would be persistent. After the excess reagent was decomposed with isopropyl alcohol, the reaction mixture was concentrated under reduced pressure. The residue was diluted with water and extracted with diethyl ether. The extract was washed with water, dried over magnesium sulfate and concentrated to give 85 mg of 1α,3β-bis(methoxycarbonyloxy)pregna-5,7-diene-20-carboxylic acid.

IR Spectrum (KBr): 1710cm$^{-1}$

EXAMPLE 7

A solution of diazomethane in diethyl ether was prepared by adding N-nitroso-N-methylurea to a mixture of 50% aqueous potassium hydroxide solution and diethyl ether in accordance with the method described in Organic Syntheses Collective Volume 2, p. 165 (1943) and this solution was added to a solution of 85 mg of 1α,3β-bis(methoxycarbonyloxy)pregna-5,7-diene-20-carboxylic acid (prepared in Example 6 above) in 5 ml of diethyl ether until the yellow color of diazomethane would be persistent. After the excess diazomethane was decomposed by addition of acetic acid, the reaction mixture was washed with aqueous sodium hydrogen carbonate solution and aqueous sodium chloride solution, dried over sodium sulfate, and concentrated. The residue was purified by silica gel column chromatography to give 79 mg of methyl 1α,3β-bis(methoxycarbonyloxy)pregna-5,7-diene-20-carboxylate.

$^1$H NMR spectrum (90 MHz) $\delta_{TMS}$CDCl$_3$: 0.72 (s, 3H), 1.03 (s, 3H), 1.19 (d, J=7 Hz, 3H), 3.64 (s, 3H), 3.77 (s, 3H), 3.79 (s, 3H), 4.6–5.2 (2H), 5.4 (m, 1H), 5.65 (m, 1H).

EXAMPLE 8

The procedure of Example 1 was repeated except that 93 mg of 1α,3β-diacetoxypregna-5,7-diene-20-carbaldehyde was used in lieu of 100 mg of 1α,3β-bis(methoxycarbonyloxy)pregna-5,7-diene-20-carbaldehyde to give 78 mg of 1α,3β-diacetoxy-20-methylpregna-5,7-diene-21-ol.

$^1$H NMR spectrum (90 MHz) $\delta_{TMS}$CDCl$_3$: 0.74 (s, 3H), 1.01 (s, 3H), 1.01 (d, J=7 Hz, 3H), 2.01 (s, 3H), 2.04 (s, 3H), 3.51 (m, 2H), 4.6–5.2 (2H), 5.38 (m, 1H), 5.64 (m, 1H).

EXAMPLE 9

The procedure of Example 1 was repeated except that 110 mg of 1α,3β-bis(t-butyldimethylsilyloxy)pregna-5,7-diene-20-carbaldehyde was used in lieu of 100 mg of 1α,3β-bis(methoxycarbonyloxy)pregna-5,7-diene-20-carbaldehyde to give 92 mg of 1α,3β-bis(t-butyldimethylsilyloxy)-20-methylpregna-5,7-dien-21-ol.

$^1$H NMR spectrum (90 MHz) $\delta_{TMS}$CDCl$_3$: 0.11 (s, 3H), 0.12 (s, 3H), 0.13 (s, 3H), 0.15 (s, 3H), 0.74 (s, 3H), 0.95 (s, 9H), 0.97 (s, 9H), 1.01 (s, 3H), 1.01 (d, J=7 Hz, 3H), 3.52 (M, 2H), 4.1–4.5 (2H), 5.38 (m, 1H), 5.64 (m, 1H).

EXAMPLE 10

The procedure of Example 1 was repeated except that 93 mg of 1α,3β-bis(methoxymethoxy)pregna-5,7-diene-20-carbaldehyde was used in lieu of 100 mg of 1α,3β-bis(methoxycarbonyloxy)pregna-5,7-diene-20-carbaldehyde to give 92 mg of 1α,3β-bis(methoxymethoxy)-20-methylpregna-5,7-dien-21-ol.

$^1$H NMR spectrum (90 MHz) $\delta_{TMS}$CDCl$_3$: 0.73 (s, 3H), 1.00 (s, 3H), 1.02 (d, J=7 Hz, 3H), 3.31 (s, 3H), 3.35 (s, 3H), 3.51 (m, 2H), 4.0–4.4 (2H), 4.7–4.9 (4H), 5.40 (m, 1H), 5.65 (m, 1H).

EXAMPLE 11

Methyl 1α,3β-bis(methoxycarbonyloxy)pregna-5,7-diene-20-carboxylate (70 mg) was added to a suspension of 10 mg of lithium aluminum hydride in 5 ml of tetrahydrofuran with ice cooling and the mixture was stirred with ice cooling for 30 minutes. The resulting reaction mixture was diluted with diethyl ether and the excess reducing agent was decomposed with a saturated aqueous solution of sodium sulfate. The insoluble matter was filtered off and washed well with ethyl acetate. The filtrate and washings were combined and concentrated. The residue was washed with cold diethyl ether to give 58 mg of 20-methylpregna-5,7-diene-1α,3β,21-triol.

$^1$H NMR spectrum (90 MHz) $\delta_{TMS}$CDCl$_3$: 0.72 (s, 3H), 1.00 (s, 3H), 1.01 (d, J=7 Hz, 3H), 3.51 (m, 2H), 3.9–4.4 (2H), 5.39 (m, 1H), 5.64 (m, 1H).

REFERENCE EXAMPLE 8

A solution of 51 mg of 20-methyl-1α,3β-bis(methoxycarbonyloxy)-21-p-toluenesulfonyloxypregna-5,7-diene in 1 ml of diethyl ether was added dropwise, at −50° C. to −60° C., to a diethyl ether solution of diisoamylcopper lithium as prepared from 100 mg of cuprous iodide and 0.9 ml of 1.1N diethyl ether solution of isoamyllithium in 2 ml of diethyl ether. reaction mixture was poured into a cold aqueous solution of ammonium chloride and the resulting mixture was extracted with diethyl ether. The extract was washed with 10% aqueous ammonia, water and an aqueous solution of sodium chloride, dried over sodium sulfate and then concentrated. The residue was dissolved in 1 ml of methanol, 10 mg of potassium carbonate was added, and the resulting mixture was stirred at ambient temperature for 12 hours. The reaction mixture was poured into water and extracted with methylene chloride. The extract was washed with an aqueous solution of sodium chloride, dried over sodium sulfate and concentrated. The residue was washed with cold ethyl acetate to give 29 mg of cholesta-5,7-diene-1α,3β-diol.

$^1$H NMR spectrum (90 MHz) $\delta_{TMS}$CDCl$_3$: 0.57 (s, 3H), 0.80 (d, J=7 Hz, 6H), 0.88 (s, 3H), 3.72 (m, 1H), 4.02 (m, 1H), 5.33 (m, 1H), 5.68 (m, 1H).

REFERENCE EXAMPLE 9

In 1 ml of tetrahydrofuran was dissolved 35 mg of 20-methyl-1α,3β-bis(methoxycarbonyloxy)-21-phenylsulfonylpregna-5,7-diene and the solution was cooled to −70° C. To the solution was added 0.8 ml of 0.1N solution of lithium hexamethyldisilazide in tetrahydrofuran. The resulting mixture was stirred for 30 minutes. After addition of 30 mg of isoamyl bromide, the mixture was stirred for 4 hours while the temperature was gradually raised to room temperature. The reaction mixture was poured into water and extracted with diethyl ether. The extract was washed with an aqueous solution of sodium hydrogen carbonate and an aqueous solution of sodium chloride, then dried over sodium sulfate and concentrated. The residue was dissolved in 1 ml of methanol and treated with 500 mg of 6% sodium amalgam in the presence of 0.5 ml of disodium hydrogen phosphate at ambient temperature for 1 hour. The reaction mixture was poured into water and extracted with diethyl ether. The extract was washed with an aqueous solution of sodium chloride, dried over sodium sulfate and concentrated. The residue was dissolved in 1 ml of methanol, 10 mg of potassium carbonate was added, and the mixture was stirred for 12 hours. The reaction mixture was then subjected to the isolation and purification procedure of Reference Example 8 to give 15 mg of cholesta-5,7-diene-1α,3β-diol which showed the same $^1$H NMR spectrum as that obtained in Reference Example 8.

EXAMPLE 12

The procedure of Example 2 was repeated except that 70 mg of 20-methyl-1α,3β-diacetoxypregna-5,7-dien-21-ol was used in lieu of 75 mg of 20-methyl-1α,3β-bis(methoxycarbonyloxy)pregna-5,7-dien-21-ol to give 68 mg of 21-bromo-20-methyl-1α,3β-diacetoxypregna-5,7-diene.

$^1$H NMR spectrum (90 MHz) $\delta_{TMS}$CDCl$_3$: 0.74 (s, 3H), 1.01 (s, 3H), 1.10 (d, J=7 Hz, 3H), 2.01 (s, 3H), 2.04 (s, 3H), 3.40 (m, 2H), 4.6–5.2 (2H), 5.38 (m, 1H), 5.64 (m, 1H).

EXAMPLE 13

The procedure of Example 2 was repeated except that 92 mg of 20-methyl-1α,3β-bis(t-butyldimethylsilyloxy)pregna-5,7-dien-21-ol was used in lieu of 75 mg of 20-methyl-1α,3β-bis(methoxycarbonyloxy)pregna-5,7-dien-21-ol to give 83 mg of 21-bromo-20-methyl-1α,3β-bis(t-butyldimethylsilyloxy)pregna-5,7-diene.

$^1$H NMR spectrum (90 MHz) $\delta_{TMS}$CDCl$_3$: 0.11 (s, 3H), 0.12 (s, 3H), 0.13 (s, 3H), 0.15 (s, 3H), 0.75 (s, 3H), 0.95 (s, 9H), 0.97 (s, 9H), 1.01 (s, 3H), 1.01 (d, J=7 Hz, 3H), 3.42 (m, 2H), 4.1–4.5 (2H), 5.38 (m, 1H), 5.64 (m, 1H).

EXAMPLE 14

The procedure of Example 2 was repeated except that 65 mg of 20-methyl-1α,3β-bis(methoxymethoxy)pregna-5,7-dien-21-ol was used in lieu of 75 mg of 20-methyl-1α,3β-bis(methoxycarbonyloxy)pregna-5,7-dien-21-ol to give 55 mg of 21-bromo-20-methyl-1α,3β-bis(methoxymethoxy)pregna-5,7-diene.

$^1$H NMR spectrum (90 MHz) $\delta_{TMS}$CDCl$_3$: 0.73 (s, 3H), 1.00 (s, 3H), 1.01 (d, J=7 Hz, 3H), 3.31 (s, 3H), 3.35 (s, 3H), 3.41 (m, 2H), 4.0–4.4 (2H), 4.7–4.9 (4H), 5.40 (m, 1H), 5.65 (m, 1H).

EXAMPLE 15

The procedure of Example 3 was repeated except that 85 mg of 20-methyl-1α,3β-diacetoxypregna-5,7-dien-21-ol was used in lieu of 81 mg of 20-methyl-1α,3β-bis(methoxycarbonyloxy)pregna-5,7-dien-21-ol to give 82 mg of 20-methyl-1α,3β-diacetoxy-21-p-toluenesulfonyloxy-pregna-5,7-diene.

$^1$H NMR spectrum (90 MHz) $\delta_{TMS}$CDCl$_3$: 0.74 (s, 3H), 1.01 (s, 3H), 1.10 (d, J=7 Hz, 3H), 2.01 (s, 3H), 2.04 (s, 3H), 2.38 (s, 3H), 3.85 (m, 2H), 4.6–5.2 (2H), 5.38 (m, 1H), 5.64 (m, 1H), 7.36 (d, J=8 Hz, 2H), 7.82 (d, J=8 Hz, 2H).

EXAMPLE 16

The procedure of Example 3 was repeated except that 101 mg of 20-methyl-1α,3β-bis(t-butyldimethylsilyloxy)pregna-5,7-dien-21-ol was used in lieu of 81 mg of 20-methyl-1α,3β-bis(methoxycarbonyloxy)pregna-5,7-dien-21-ol to give 99 mg of 20-methyl-1α,3β-bis(t-butyldimethylsilyloxy)-21-p-toluenesulfonyloxypregna-5,7-diene.

$^1$H NMR spectrum (90 MHz) $\delta_{TMS}$CDCl: 0.11 (s, 3H), 0.12 (s, 3H), 0.13 (s, 3H), 0.15 (s, 3H), 0.75 (s, 3H), 0.95 (s, 9H), 0.97 (s, 9H), 1.01 (s, 3H), 1.01 (d, J=7 Hz, 3H), 2.40 (s, 3H), 3.83 (m, 2H), 4.1–4.5 (2H), 5.38 (m, 1H), 5.64 (m, 1H), 7.36 (d, J=8 Hz, 2H), 7.82 (d, J=8 Hz, 2H).

EXAMPLE 17

The procedure of Example 3 was repeated except that 75 mg of 20-methyl-1α,3β-bis(methoxymethoxy)-pregna-5,7-dien-21-ol was used in lieu of 81 mg of 20-methyl-1α,3β-bis(methoxycarbonyloxy)pregna-5,7-dien-21-ol to give 78 mg of 20-methyl-1α,3β-bis(methoxymethoxy)-21-p-toluenesulfonyloxypregna-5,7-diene.

$^1$H NMR spectrum (90 MHz) $\delta_{TMS}$CDCl$_3$: 0.73 (s, 3H), 1.00 (s, 3H), 1.01 (d, J=7 Hz, 3H), 2.38 (s, 3H), 3.31 (s, 3H), 3.35 (s, 3H), 3.83 (m, 2H), 4.0–4.4 (2H), 4.7–4.9 (4H), 5.40 (m, 1H), 5.65 (m, 1H), 7.36 (d, J=8 Hz, 2H), 7.82 (d, J=8 Hz, 2H).

EXAMPLE 18

To a solution of 20 mg of sodium metaperiodate in 2 ml of tetrahydrofuran was added dropwise an ice-cooled solution of 41 mg of 20-methyl-1α,3β-bis(methoxycarbonyloxy)-21-phenylthiopregna-5,7-diene in 1 ml of diethyl ether. The resulting mixture was stirred with ice cooling for 30 minutes, then the insoluble matter was filtered off and washed with diethyl ether, and the filtrate and washings were combined, washed in sequence with an aqueous solution of sodium thiosulfate, water, an aqueous solution of sodium hydrogen carbonate and an aqueous solution of sodium chloride, then dried and concentrated. The residue was purified by silica gel column chromatography to give 29 mg of 20-methyl-1α,3β-bis(methoxycarbonyloxy)-21-phenylsulfinylpregna-5,7-diene.

$^1$H NMR spectrum (90 MHz) $\delta_{TMS}$CDCl$_3$: 0.70 (s, 3H), 0.95 (d, J=7 Hz, 3H), 1.00 (s, 3H), 3.12 (m, 2H), 3.76 (s, 3H), 3.79 (s, 3H), 4.6–5.2 (2H), 5.38 (m, 1H), 5.64 (m, 1H), 7.2–7.9 (5H).

EXAMPLE 19

The procedure of Example 5 was repeated except that 59 mg of 21-bromo-20-methyl-1α,3β-diacetoxypregna-5,7-diene was used in lieu of 65 mg of 21-bromo-20-methyl-1α,3β-bis(methoxycarbonyloxy)pregna-5,7-diene to give 45 mg of 20-methyl-1α,3β-diacetoxy-21-phenylsulfonyl-pregna-5,7-diene.

$^1$H NMR spectrum (90 MHz) $\delta_{TMS}$CDCl$_3$: 0.74 (s, 3H), 1.01 (s, 3H), 1.10 (d, J=7 Hz, 3H), 2.01 (s, 3H), 2.04 (s, 3H), 3.10 (m, 2H), 4.6–5.2 (2H), 5.38 (m, 1H), 5.64 (m, 1H), 7.4–8.1 (5H).

EXAMPLE 20

The procedure of Example 5 was repeated except that 78 mg of 21-bromo-20-methyl-1α,3β-bis(t-butyldimethylsilyloxy)pregna-5,7-diene was used in lieu of 65 mg of 21-bromo-20-methyl-1α,3β-bis(methoxycarbonyloxy)pregna-5,7-diene to give 63 mg of 20-methyl-1α,3β-bis(t-butyldimethylsilyloxy)-21-phenylsulfonyl-pregna-5,7-diene.

$^1$H NMR spectrum (90 MHz) $\delta_{TMS}$CDCl$_3$: 0.11 (s, 3H), 0.12 (s, 3H), 0.13 (s, 3H), 0.15 (s, 3H), 0.75 (s, 3H), 0.95 (s, 9H), 0.97 (s, 9H), 1.01 (s, 3H), 1.01 (d, J=7 Hz, 3H), 3.10 (m, 2H), 4.1–4.5 (2H), 5.38 (m, 1H), 5.64 (m, 1H), 7.4–8.1 (5H).

EXAMPLE 21

The procedure of Example 5 was repeated except that 59 mg of 21-bromo-20-methyl-1α,3β-bis(methoxymethoxy)pregna-5,7-diene and 95 mg of sodium p-toluenesulfinate were used in lieu of 65 mg of 21-bromo-20-methyl-1α,3β-bis(methoxycarbonyloxy) pregna-5,7- diene and 80 mg of sodium benzenesulfinate, respectively, to give 43 mg of 20-methyl-1α,3β-bis(methoxymethoxy)-21-p-tolylsulfonylpregna-5,7-diene.

¹H NMR spectrum (90 MHz) δ$_{TMS}$CDCl$_3$: 0.73 (s, 3H), 1.00 (s, 3H), 1.01 (d, J=7 Hz, 3H), 2.48 (s, 3H), 3.10 (m, 2H), 3.31 (s, 3H), 3.35 (s, 3H), 4.0–4.4 (2H), 4.7–4.9 (4H), 5.40 (m, 1H), 5.65 (m, 1H), 7.4–8.1 (4H).

EXAMPLE 22

The procedure of Example 6 was repeated except that 105 mg of 1α,3β-diacetoxypregna-5,7-diene-20-carbaldehyde was used in lieu of 120 mg of 1α,3β-bis(methoxycarbonyloxy)pregna-5,7-diene-20-carbaldehyde to give 89 mg of 1α,3β-diacetoxypregna-5,7-diene-20-carboxylic acid.

IR spectrum (KBr): 1710 cm$^{-1}$

EXAMPLE 23

The procedure of Example 6 was repeated except that 140 mg of 1α,3β-bis(t-butyldimethylsilyloxy)pregna-5,7-diene-20-carbaldehyde was used in lieu of 120 mg of 1α,3β-bis(methoxycarbonyloxy)pregna-5,7-diene-20-carbaldehyde to give 112 mg of 1α,3β-bis(t-butyldimethylsilyloxy)pregna-5,7-diene-20-carboxylic acid.

IR spectrum (KBr): 1710 cm$^{-1}$

EXAMPLE 24

The procedure of Example 6 was repeated except that 105 mg of 1α,3β-bis(methoxymethoxy)pregna-5,7-diene-20-carbaldehyde was used in lieu of 120 mg of 1α,3β-bis(methoxycarbonyloxy)pregna-5,7-diene-20-carbaldehyde to give 80 mg of 1α,3β-bis(methoxymethoxy)pregna-5,7-diene-20-carboxylic acid.

IR spectrum (KBr): 1710 cm$^{-1}$

EXAMPLE 25

The procedure of Example 7 was repeated except that 89 mg of 1α,3β-diacetoxypregna-5,7-diene-20-carboxylic acid obtained in Example 22 was used in lieu of 85 mg of 1α,3β-bis(methoxycarbonyloxy)pregna-5,7-diene-20-carboxylic acid to give 82 mg of methyl 1α,3β-di-acetoxypregna-5,7-diene-20-carboxylate.

¹H NMR spectrum (90 MHz) δ$_{TMS}$CDCl$_3$: 0.72 (s, 3H), 1.02 (s, 3H), 1.15 (d, J=7 Hz, 3H), 2.00 (s, 3H), 2.05 (s, 3H), 3.64 (s, 3H), 4.62–5.2 (2H), 5.40 (m, 1H), 5.65 (m, 1H).

EXAMPLE 26

The procedure of Example 7 was repeated except that 112 mg of 1α,3β-bis(t-butyldimethylsilyloxy)pregna-5,7-diene-20-carboxylic acid obtained in Example 23 was used in lieu of 85 mg of 1α,3β-bis(methoxycarbonyloxy)pregna-5,7-diene-20-carboxylic acid to give 91 mg of methyl 1α,3β-bis(t-butyldimethylsilyloxy)pregna-5,7-diene-20-carboxylate.

¹H NMR spectrum (90 MHz) δ$_{TMS}$CDCl$_3$: 0.11 (s, 3H), 0.12 (s, 6H), 0.13 (s, 3H), 0.74 (s, 3H), 0.95 (s, 9H), 0.97 (s, 9H), 1.01 (s, 3H), 1.01 (d, J=7 Hz, 3H), 3.64 (s, 3H), 4.1–4.5 (2H), 5.38 (m, 1H), 5.64 (m, 1H).

EXAMPLE 27

The procedure of Example 7 was repeated except that 80 mg of 1α,3β-bis(methoxymethoxy)pregna-5,7-diene-20-carboxylic acid obtained in Example 24 was used in lieu of 85 mg of 1α,3β-bis(methoxycarbonyloxy)pregna-5,7-diene-20-carboxylic acid to give 65 mg of methyl 1α,3β-bis(methoxymethoxy)pregna-5,7-diene-20-carboxylate.

¹H NMR spectrum (90 MHz) δ$_{TMS}$CDCl$_3$: 0.72 (s, 3H), 0.92 (s, 3H), 1.14 (d, J=7 Hz, 3H), 3.30 (s, 3H), 3.34 (s, 3H), 3.64 (s, 3H), 4.0–4.4 (2H), 4.75–4.85 (4H), 5.39 (m, 1H), 5.65 (m, 1H).

EXAMPLE 28

In 2 ml of tetrahydrofuran was dissolved 50 mg of 1α,3β-bis(methoxycarbonyloxy)-20-methyl-21-phenylsulfonylpregna-5,7-diene and the solution was cooled in a dry ice-acetone bath in an argon atmosphere. To the solution was added 0.4 ml of a solution of lithium diisopropylamide prepared from 2 ml of a 1.5N solution of butyllithium in hexane and 0.5 ml of diisopropylamine in 10 ml of tetrahydrofuran, and the resulting mixture was stirred at −30° C. for 30 minutes and then again cooled in a dry ice-acetone bath. A solution of 150 mg of isovaleraldehyde in 1 ml of tetrahydrofuran was added and the mixture was stirred for 4 hours while the mixture was gradually warmed to −30° C. A saturated aqueous solution of ammonium chloride was added to the reaction mixture and the mixture was allowed to warm to ambient temperature. Diethyl ether was added to the reaction mixture and the organic layer was separated, the aqueous layer was extracted with diethyl ether. The organic layer was combined, washed in sequence with an aqueous solution of sodium hydrogen carbonate and an aqueous solution of sodium chloride, then dried over sodium sulfate and concentrated. The residue was purified by silica gel column chromatography to give 28 mg of 1α,3β-bis(methoxycarbonyloxy)-22-phenylsulfonylcholesta-5,7-dien-23-ol.

¹H NMR spectrum (90 MHz) δ$_{TMS}$CDCl$_3$: 0.64 (s, 3H), 0.80–1.02 (12H), 3.53 (m, 1H), 3.64 (s, 3H), 3.70 (s, 3H), 3.79 (m, 1H), 4.4–4.9 (2H), 5.30 (m, 1H), 5.58 (m, 1H), 7.6–8.1 (5H).

EXAMPLE 29

In 400 ml of diethyl ether was dissolved 28 mg of 1α,3β-bis(methoxycarbonyloxy)-22-phenylsulfonylcholesta-5,7-dien -23-ol and the solution was cooled in an ice bath while argon was passing through the solution. This solution was irradiated with ultraviolet light for 5 minutes using a 400 W high pressure mercury lamp. The reaction mixture was concentrated under reduced pressure and the residue was purified by silica gel column chromatography to give 6 mg of 1',3β-bis(methoxycarbonyloxy)-22-phenylsulfonyl-9,10-secocholesta5(10),6,8-trien-23-ol. This was dissolved in 2 ml of ethanol and the solution was heated under reflux for 2 hours under argon atmosphere. The reaction mixture was cooled and then concentrated under reduced pressure and the residue was purified by silica gel thin layer chromatography to give 4.8 mg of 1α,3β-bis(methoxycarbonyloxy)-22-phenylsulfonyl-9,10-secocholesta-5,7, 10(19)-trien-23-ol having the following physical characteristics:

¹H NMR spectrum (90 MHz) δ$_{TMS}$CDCl$_3$: 0.55 (s, 3H), 0.90 (d, J=7 Hz, 9H), 3.54 (m, 1H), 3.66 (s, 3H), 3.68 (s, 3H), 3.79 (m, 1H), 4.5–5.1 (3H), 5.28 (br. s, 1H), 5.95 (d, J=11 Hz, 1H), 6.24 (d, J=11 Hz, 1H), 7.6–8.1 (5H).

EXAMPLE 30

To a solution of 4.8 mg of 1α,3β-bis (methoxycarbonyloxy)-22-phenylsulfonyl-9,10-secocholesta-5,7, 10(19)-trien-23-ol in 3 ml of methanol was added 10 mg of potassium carbonate and the mixture was stirred overnight at ambient temperature. The reaction mixture was concentrated under reduced pressure and the residue was purified by silica gel thin layer chromatography to give 3.2 mg of 22-phenylsulfonyl-9,10-secocholesta-5,7,10(19)-triene-1α,3β,23-triol.

$^1$H NMR spectrum (90 MHz) $\delta_{TMS}$CDCl$_3$: 0.58 (s, 3H), 0.94 (d, J=6 Hz, 9H), 3.52 (m, 1H), 3.80 (m, 1H), 4.2–4.6 (2H), 4.98 (br. s, 1H), 5.13 (br. s, 1H), 5.90 (d, J=11 Hz, 1H), 6.30 (d, J=11 Hz, 1H), 7.6–8.1 (5H).

REFERENCE EXAMPLE 10

To a solution of 3.2 mg of 22-phenylsulfonyl-9,10-secocholesta-5,7,10(19)-triene-1α,3β,23-triol in 1 ml of methanol was added 0.25 g of disodium hydrogen phosphate, followed by the addition of 0.8 g of 5% sodium amalgam, and the mixture was stirred under argon atmosphere for 30 minutes. The reaction mixture was diluted with methanol and the insoluble matter was filtered off and washed with methanol. The filtrate and washings were combined and concentrated under reduced pressure and the residue was purified by silica gel thin layer chromatography to give 1.8 mg of 9,10-secocholesta-5,7,10(19)-triene-1α,3β,23-triol.

$^1$H NMR spectrum (90 MHz) $\delta_{TMS}$CDCl$_3$: 0.58 (s, 3H), 0.96 (d, J=7 Hz, 9H), 3.79 (m, 1H), 4.1–4.5 (2H), 5.00 (br. s, 1H), 5.32 (br. s, 1H), 6.03 (d, J=11 Hz, 1H), 6.39 (d, J=11 Hz, 1H).

UV spectrum (ethanol) λmax: 265 nm.

Mass spectrum (FD): 416 (M+).

EXAMPLE 31

In 2 ml of tetrahydrofuran was dissolved 45 mg of 20-methyl-1α,3β-diacetoxy-21-phenylsulfonylpregna-5,7-diene and the solution was cooled in a dry ice-acetone bath under argon atmosphere. A 0.35-ml portion of a lithium diisopropylamide solution prepared from 2 ml of a 1.5N hexane solution of butyllithium and 0.5 ml of diisopropylamine in 10 ml of tetrahydrofuran was added and the resulting mixture was stirred at −30° C. for 30 minutes. The mixture was again cooled in a dry ice-acetone bath and then a solution of 150 mg of 1,2-epoxy-3-methylbutane in 1 ml of tetrahydrofuran was added, and the resulting mixture was stirred at −30° C. to −20° C. for 6 hours. A saturated aqueous solution of ammonium chloride was added to the reaction mixture and the mixture was allowed to warm to ambient temperature. Diethyl ether was then added to the reaction mixture, the organic layer was separated, and the aqueous layer was extracted with diethyl ether. The organic layer was combined, washed in sequence with an aqueous solution of sodium hydrogen carbonate and an aqueous solution of sodium chloride, then dried over sodium sulfate and concentrated. The residue was purified by silica gel thin layer chromatography to give 21 mg of 1α,3β-diacetoxy-22-phenylsulfonylcholesta-5,7-dien-24-ol.

$^1$H NMR spectrum (90 MHz) $\delta_{TMS}$CDCl$_3$: 0.63 (s, 3H), 0.94 (d, J=7 Hz, 3H), 0.98 (d, J=7 Hz, 6H), 2.01 (s, 3H), 2.04 (s, 3H), 3.48 (m, 1H), 3.75 (m, 1H), 4.4–4.9 (2H), 5.30 (m, 1H), 5.58 (m, 1H), 7.6–8.1 (5H).

EXAMPLE 32

In 350 ml of diethyl ether was dissolved 21 mg of 1α,3β-diacetoxy-22-phenylsulfonylcholesta-5,7-dien-24-ol and the solution was cooled in an ice bath while argon gas was passing through the solution. This solution was then irradiated with ultraviolet light for 5 minutes using a 400 W high pressure mercury lamp. The reaction mixture was concentrated under reduced pressure and the residue was purified by silica gel thin layer chromatography to give 3.2 mg of 1α,3β-diacetoxy-22-phenylsulfonyl-9,10-secocholesta-5(10),6,8-trien-24-ol. This was dissolved in 1.5 ml of ethanol and the solution was heated under reflux for 2 hours under argon atmosphere. After cooled to ambient temperature, the reaction mixture was concentrated under reduced pressure. The residue was purified by silica gel thin layer chromatography to give 2.1 mg of 1α,3β-diacetoxy-22-phenylsulfonyl-9,10-secocholesta-5,7,10(19)-trien-24-ol.

$^1$H NMR spectrum (90 MHz) $\delta_{TMS}$CDCl$_3$: 0.56 (s, 3H), 0.91 (d, J=6 Hz, 3H), 0.93 (d, J=7 Hz, 6H), 2.00 (s, 3H), 2.05 (s, 3H), 3.24 (m, 1H), 3.50 (m, 1H), 4.5–5.1 (3H), 5.29 (br. s, 1H), 5.97 (d, J=11 Hz, 1H), 6.30 (d, J=11 Hz, 1H), 7.5–8.1 (5H).

EXAMPLE 33

To a solution of 2.1 mg of 1α,3β-diacetoxy-22-phenyl-sulfonyl-9,10-secocholesta-5,7,10(19)-trien-24-ol in 2 ml of methanol was added 5 mg of potassium carbonate and the mixture was stirred overnight at ambient temperature. The reaction mixtrue was concentrated under reduced pressure and the concentrate was purified by silica gel thin layer chromatography to give 1.1 mg of 22-phenylsulfonyl-9,10-secocholesta-5,7,10(19)-triene-1α,3β,24-triol.

$^1$H NMR spectrum (90 MHz) $\delta_{TMS}$CDCl$_3$: 0.57 (s, 3H), 0.87 (d, J=7 Hz, 6H), 0.96 (d, J=6 Hz, 3H), 3.19 (m, 1H), 3.52 (m, 1H), 4.1–4.5 (2H), 4.85 (br. s, 1H), 5.30 (br. s, 1H), 6.05 (d, J=11 Hz, 1H), 6.27 (d, J=11 Hz, 1H), 7.6–8.1 (5H).

REFERENCE EXAMPLE 11

To a solution of 1.1 mg of 22-phenylsulfonyl-9,10-secocholesta-5,7,10(19)-triene-1a,38,24-triol in 1 ml of methanol was added 0.25 g of disodium hydrogen phosphate, followed by the addition of 0.8 g of 5% sodium amalgam, and the mixture was stirred under argon atmosphere for 30 minutes. The reaction mixture was diluted with methanol and the insoluble matter was filtered off and washed with methanol. The filtrate and washings were combined and concentrated under reduced pressure and the residue was purified by silica gel thin layer chromatography to give 0.2 mg of 9,10-secocholesta-5,7,10(19)-triene-1α,3β,24-triol.

$^1$H NMR spectrum (90 MHz) $\delta_{TMS}$CDCl$_3$: 0.58 (s, 3H), 0.88 (d, J=7 Hz, 6H), 0.95 (d, J=6 Hz, 3H), 3.19 (m, 1H), 4.1–4.5 (2H), 4.90 (br. s, 1H), 5.32 (br. s, 1H), 6.00 (d, J=11 Hz, 1H), 6.30 (d, J=11 Hz, 1H).

UV spectrum (ethanol) λmax: 266 nm.

Mass spectrum (FD): 416 (M+).

EXAMPLE 34

In 2 ml of tetrahydrofuran was dissolved 63 mg of 20-methyl-1α,3β-bis(t-butyldimethylsilyloxy)-21-phenyl-sulfonylpregna-5,7-diene and the solution was cooled in a dry ice-acetone bath under argon atmosphere. A 0.45-ml portion of a lithium diisopropylamide solution prepared from 2 ml of a 1.5N hexane solution of butyllithium and 0.5 ml of diisopropylamine in 10 ml of tetrahydrofuran was added and the resulting mixture was stirred at −30° C. for 30 minutes. The mixture was again cooled in a dry ice-acetone bath, a solution of 140 mg of 4-bromo-2-methyl-2-(2-tetrahydropyranyloxy)-butane in 1 ml of tetrahydrofuran was then added, and the mixture was stirred for 5 hours while the reaction mixture was warmed gradually to −20° C. A saturated aqueous solution of ammonium chloride was added to the reaction mixture and the mixture was allowed to warm to ambient temperature. Diethyl ether was added to the reaction mixture, the organic layer was separated, and the aqueous layer was extracted with diethyl ether. The organic layer was combined, washed in sequence with an aqueous solution of sodium hydrogen carbonate and an aqueous solution of sodium chloride, then dried over sodium sulfate and concentrated. The residue was purified by silica gel thin layer chromatography to give 54 mg of 1α,3β-bis(t-butyldimethylsilyloxy)-22-phenyl-sulfonyl-25-(2-tetrahydropyranyloxy)cholesta-5,7-diene.

$^1$H NMR spectrum (90 MHz) $\delta_{TMS}$CDCl$_3$: 0.11 (s, 3H), 0.12 (s, 3H), 0.13 (s, 3H), 0.15 (s, 3H), 0.69 (s, 3H), 0.90 (d, J=7 Hz, 3H), 0.95 (s, 9H), 0.97 (s, 9H), 1.00 (s, 3H), 1.16 (s, 3H), 1.17 (s, 3H), 3.56 (m, 1H), 4.1–4.5 (3H), 5.37 (m, 1H), 5.65(m, 1H), 7.4–8.1 (5H).

EXAMPLE 35

In 400 ml of diethyl ether was dissolved 54 mg of 1α,3β-bis(t-butyldimethylsilyloxy)-22-phenylsulfonyl-25-(2-tetrahydropyranyloxy)cholesta-5,7-diene and the solution was cooled in an ice bath while argon gas was passing through the solution. This solution was irradiated with ultraviolet light for 5 minutes using a 400 W high pressure mercury lamp. The reaction mixture was concentrated under reduced pressure and the residue was purified by silica gel column chromatography to give 9.2 mg of 1α,3β-bis(t-butyldimethylsilyloxy)-22-phenylsulfonyl-25-(2-tetrahydropyranyloxy)-9, 10-secocholesta-5(10),6,8-triene. This was dissolved in 3 ml of ethanol and the solution was heated under reflux under argon atmosphere for 2 hours. After cooled to ambient temperature, the reaction mixture was concentrated under reduced pressure. The residue was purified by silica gel thin layer chromatography to give 7.5 mg of 1α,3β-bis(t-butyldimethylsilyloxy)-22-phenylsulfonyl-25-(2-tetrahydropyranyloxy)-9,10-secocholesta-5,7,10(19)-triene having the physical characteristics shown below.

$^1$H NMR spectrum (90 MHz) $\delta_{TMS}$CDCl$_3$: 0.00 (s, 12H), 0.55 (s, 3H), 0.85 (s, 18H), 1.15 (s, 3H), 1.17 (s, 3H), 3.50 (m, 1H), 4.1–4.5 (3H), 4.84 (br. s, 1H), 5.16 (br. s, 1H), 6.00 (d, J=11 Hz, 1H), 6.21 (d, J=11 Hz, 1H), 7.6–8.1 (5H).

EXAMPLE 36

To 7.5 mg of 1α,3β-bis(t-butyldimethylsilyloxy)-22-phenylsulfonyl-25-(2-tetrahydropyranyloxy)-9, 10-secocholesta-5,7,10(19)-triene was added 2 ml of an acetic acid-water-tetrahydrofuran mixture (3:1:1 by volume). The mixture was stirred at room temperature for 12 hours. The reaction mixture was diluted with water and extracted with methylene chloride. The extract was washed with an aqueous solution of sodium hydrogen carbonate and an aqueous solution of sodium chloride, then, dried over sodium sulfate and concentrated. The residue was purified by silica gel thin layer chromatography to give 4.8 mg of 22-phenyl-sulfonyl-9,10-secocholesta-5,7,10(19)-triene-1α,3β,25 -triol.

$^1$H NMR spectrum (90 MHz) $\delta_{TMS}$CDCl$_3$: 0.60 (s, 3H), 1.01 (d, J=5 Hz, 3H), 1.18 (s, 6H), 3.48 (m, 1H), 4.1–4.6 (2H), 4.93 (br. s, 1H), 5.35 (br. s, 1H), 6.18 (d, J=11 Hz, 1H), 6.35 (d, J=11 Hz, 1H), 7.6–8.1 (5H).

REFERENCE EXAMPLE 12

To a solution of 4.8 mg of 22-phenylsulfonyl-9,10-secocholesta-5,7,10(19)-triene-1α,3β,25-triol in 2 ml of methanol was added 0.25 g of disodium hydrogen phosphate, followed by the addition of 0.8 g of 5% sodium amalgam, and the mixture was stirred under argon atmosphere for 45 minutes. The reaction mixture was diluted with methanol and the insoluble matter was filtered off and washed with methanol. The filtrate and washings were combined and concentrated under reduced pressure and the residue was purified by silica gel thin layer chromatography to give 1.9 mg of 9,10-seco-cholesta-5,7,10(19)-triene-1α,3β,25-triol.

$^1$H NMR spectrum (90 MHz) $\delta_{TMS}$CDCl$_3$: 0.58 (s, 3H), 1.00 (d, J=6 Hz, 3H), 1.18 (s, 6H), 4.1–4.6 (2H), 4.95 (br. s, 1H), 5.40 (br. s, 1H), 6.15 (d, J=11 Hz, 1H), 6.30 (d, J=11 Hz, 1H).

UV spectrum (ethanol) λmax: 264 nm.

Mass spectrum (FD) : 416 (M+).

EXAMPLE 37

In 2 ml of tetrahydrofuran was dissolved 71 mg of 20-methyl-1α,3β-bis(t-butyldimethylsilyloxy)-21-phenylsulfonylpregna-5,7-diene and the solution was cooled in a dry ice-acetone bath under argon atmosphere. To the solution was added a 0.4-ml portion of a lithium diisopropylamide solution prepared from 2 ml of a 1.5N hexane solution of butyllithium and 0.5 ml of diisopropylamine in 10 ml of tetrahydrofuran. The resulting mixture was stirred at −30° C. for 30 minutes. The mixutre was again cooled in a dry ice-acetone bath, a solution of 120 mg of 3-methyl-3-(2-tetrahydropyranyloxy)butanal in 1 ml of tetrahydrofuran was added, and the resulting mixture was stirred at −50° C. for 5 hours. A saturated aqueous solution of ammonium chloride was added to the reaction mixture and the mixture was allowed to warm to ambient temperature. Diethyl ether was added to the reaction mixture, the organic layer was separated, and the aqueous layer was extracted with diethyl ether. The organic layer was combined, washed in sequence with an aqueous solution of sodium hydrogen carbonate and an aqueous solution of sodium chloride, then dried over sodium sulfate and concentrated. The residue was purified by silica gel column chromatography to give 68 mg of 1α,3β-bis(t-butyldimethylsilyloxy)-22-phenylsulfonyl-25-(2 -tetrahydropyranyloxy)cholesta-5,7-dien-23-ol.

$^1$H NMR spectrum (90 MHz) $\delta_{TMS}$CDCl$_3$: 0.05 (s, 3H), 0.06 (s, 6H), 0.11 (s, 3H), 0.72 (s, 3H), 0.88 (s, 9H), 0.90 (d, J=7 Hz, 3H), 0.90 (s, 9H), 1.00 (s, 3H), 1.16 (s, 3H), 1.17 (s, 3H), 3.55 (m, 1H), 3.75 (m, 1H) 4.1–4.5 (3H), 5.40 (m, 1H), 5.65 (m, 1H), 7.6–8.1 (5H).

EXAMPLE 38

In 400 ml of diethyl ether was dissolved 68 mg of 1α,3β-bis(t-butyldimethylsilyloxy)-22-phenylsulfonyl-25-(2-tetrahydropyranyloxy)cholesta-5,7-dien-23 -ol and the solution was cooled in an ice bath while argon gas was passing through the solution. This solution was irradiated with ultraviolet light for 5 minutes using a 400 W high pressure mercury lamp. The reaction mixture was concentrated under reduced pressure and the residue was purified by silica gel column chromatography to give 10.5 mg of 1α,3β-bis(t-butyldimethyl-silyloxy)-22-phenylsulfonyl-25-(2-tetrahydropyranyloxy)-9, 10-secocholesta-5(10),6,8-trien-23-ol. This was dissolved in 3 ml of ethanol and the solution was heated under reflux in an argon atmosphere for 2 hours. After cooling, the reaction mixture was concentrated under reduced pressure and the residue was purified by silica gel thin layer chromatography to give 8.2 mg of 1α,3β- bis(t-butyldimethylsilyloxy)-22-phenylsulfonyl-25-(2-tetrahydropyranyloxy)-9,10-secocholesta-5,7,10,(19)-trien-23-ol having the physical characteristics shown below.

$^1$H NMR spectrum (90 MHz) $\delta_{TMS}$CDCl$_3$: 0.05 (s, 12H), 0.56 (s, 3H), 0.87 (s, 18H), 1.00 (d, J=6 Hz, 3H), 1.13 (s, 3H), 1.16 (s, 3H), 3.51 (m, 1H), 3.70 (m, 1H), 4.1–4.6 (3H), 4.86 (br. s, 1H), 5.18 (br. s, 1H), 6.03 (d, J=11 Hz, 1H), 6.25 (d, J=11 Hz, 1H), 7.5–8.1 (5H).

EXAMPLE 39

To 8.2 mg of 1α,3β-bis(t-butyldimethylsilyloxy)-22-phenylsulfonyl-25-(2-tetrahydropyranyloxy)-9,10-secocholesta-5,7,10(19)-trien-23-ol was added 2 ml of an acetic acid-water-tetrahydrofuran mixture (3:1:1 by volume). The resulting mixture was stirred at room temperature for 12 hours. The reaction mixture was diluted with water and extracted with methylene chloride. The extract was washed with an aqueous solution of sodium hydrogen carbonate and an aqueous solution of sodium chloride, then dried over sodium sulfate and concentrated. The residue was purified by silica gel thin layer chromatography to give 4.3 mg of 22-phenylsulfonyl-9,10-secocholesta-5,7,10(19)-triene-1α,3β, 23,25-tetraol.

$^1$H NMR spectrum (90 MHz) $\delta_{TMS}$CDCl$_3$ : 0.59 (s, 3H), 1.01 (d, J=7 Hz, 3H), 1.17 (s, 6H), 3.4–3.8 (2H), 3.5–4.1 (3H), 4.1–4.6 (2H), 4.92 (br. s, 1H), 5.33 (br. s, 1H), 6.02 (d, J=11 Hz, 1H), 6.32 (d, J=11 Hz, 1H), 7.5–8.1 (5H).

REFERENCE EXAMPLE 13

To a solution of 4.3 mg of 22-phenylsulfonyl-9,10-secocholesta-5,7,10(19)-triene-1α,3β,23,25 -tetraol in 2 ml of methanol was added 0.25 g of disodium hydrogen phosphate, followed by the addition of 0.8 g of 5% sodium amalgam, and the mixture was stirred under argon atmosphere for 30 minutes. The reaction mixture was diluted with methanol and the insoluble matter was filtered off and washed with methanol. The filtrate and washings were combined and concentrated under reduced pressure and the residue was purified by silica gel thin layer chromatography to give 1.9 mg of 9,10-secocholesta-5,7,10(19)-triene-1α,3β,23,25-tetraol.

$^1$H NMR spectrum (90 MHz) $\delta_{TMS}$CDCl$_3$: 0.59 (s, 3H), 0.99 (d, J=6 Hz, 3H), 1.17 (s, 6H), 3.6–4.5 (3H), 4.98 (br. s, 1H), 5.35 (br. s, 1H), 6.10 (d, J=11 Hz, 1H), 6.30 (d, J=11 Hz, 1H).

UV spectrum (ethanol) λmax: 265 nm. Mass spectrum (FD) : 432 (M+).

EXAMPLE 40

In 2 ml of tetrahydrofuran was dissolved 43 mg of 20-methyl-1α,3β-bis(methoxymethoxy)-21-p-tolylsulfonylpregna-5,7-diene and the solution was cooled in a dry ice-acetone bath under argon atmosphere. To the solution was added 0.35 ml of a lithium diisopropylamide solution prepared from 2 ml of a 1.5N hexane solution of butyllithium and 0.5 ml of diisopropylamine in 10 ml of tetrahydrofuran. The mixture was stirred at −30° C. for 30 minutes and then again cooled in a dry ice-acetone bath. A solution of 100 mg of 1,2-epoxy-3-methyl-3-(2-tetrahydropyranyloxy)butane in 1 ml of tetrahydrofuran was added and the resulting mixture was stirred at −20° C. for 7 hours. A saturated aqueous solution of ammonium chloride was added to the reaction mixture and the mixture was allowed to warm to ambient temperature. Diethyl ether was added to the reaction mixture, the organic layer was separated, and the aqueous layer was extracted with diethyl ether. The organic layer was combined, washed in sequence with an aqueous solution of sodium hydrogen carbonate and an aqueous solution of sodium chloride, then dried over sodium sulfate and concentrated. The residue was purified by silica gel column chromatography to give 38 mg of 1α,3β-bis-(methoxymethoxy)-22-p-tolylsulfonyl-25-(2 -tetrahydropyranyloxy)cholesta-5,7-dien-24-ol.

$^1$H NMR spectrum (90 MHz) $\delta_{TMS}$CDCl$_3$: 0.72 (s, 3H), 0.92 (d, J=6 Hz, 3H), 1.01 (s, 3H), 1.17 (s, 3H), 1.20 (s, 3H), 2.47 (s, 3H), 3.23 (m, 1H), 3.31 (s, 3H), 3.35 (s, 3H), 3.55 (m, 1H), 4.0–4.5 (3H), 4.7–4.9 (4H), 5.42 (m, 1H), 5.65 (m, 1H), 7.6–8.1 (4H).

EXAMPLE 41

In 400 ml of diethyl ether was dissolved 38 mg of 1α,3β-bis(methoxymethoxy)-22-p-tolysulfonyl-25-(2-tetrahydropyranyloxy)cholesta-5,7-dien-24-ol and the solution was cooled in an ice bath while argon gas was passing through the solution. This solution was then irradiated with ultraviolet light for 5 minutes using a 400 W high pressure mercury lamp. The reaction mixture was concentrated under reduced pressure and the residue was purified by silica gel column chromatography to give 6.3 mg of 1α,3β-bis(methoxymethoxy)-22-p-tolylsulfonyl-25-(2-tetrahydropyranyloxy)-9,10 -secocholesta-5(10),6,8-trien-24-ol. This was dissolved in 2 ml of ethanol and the solution was heated under reflux under argon atmosphere for 2 hours. After cooled to ambient temperature, the reaction mixture was concentrated under reduced pressure. Purification of the residue by silica gel thin layer chromatography gave 3.9 mg of 1α,3β-bis(methoxymethoxy)-22-p-tolysulfonyl-25-(2-tetrahydropyranyloxy)-9,10-secocholesta-5,7,10(19)-trien-24-ol having the physical characteristics shown below.

$^1$H NMR spectrum (90 MHz) $\delta_{TMS}$CDCl$_3$: 0.58 (s, 3H), 1.15 (s, 3H), 1.20 (s, 3H), 2.47 (s, 3H), 3.25 (m, 1H), 3.30 (s, 3H), 3.32 (s, 3H), 3.55 (m, 1H), 4.0–4.5 (3H), 4.7–4.9 (5H), 5.20 (br. s, 1H), 6.00 (d, J=11 Hz, 1H), 6.28 (d, J=11 Hz, 1H), 7.5–8.1 (4H).

EXAMPLE 42

To a solution 3.9 mg of 1α,3β-bis(methoxymethoxy)-22-p-tolylsulfonyl-25-(2-tetrahydropyranyloxy)-9,10 -secocholesta-5,7,10(19)-trien-24-ol in 1 ml of methanol was added 1 ml of 1N hydrochloric acid and the mixture was stirred overnight at ambient temperature. The reaction mixture was neutralized by addition of an aqueous solution of sodium hydrogen carbonate and then concentrated under reduced pressure. Purification of the residue by silica gel thin layer chromatography gave 1.7 mg of 22-p-tolylsulfonyl-9,10-secocholesta-5,7,10(19)-triene-1α,3β,24,25-tetraol.

$^1$H NMR spectrum (90 MHz) $\delta_{TMS}$CDCl$_3$: 0.58 (s, 3H), 1.12 (s, 6H), 2.48 (s, 3H), 3.25 (m, 1H), 3.55 (m, 1H), 4.1–4.5 (2H), 4.93 (br. s, 1H), 5.30 (br. s, 1H), 6.02 (d, J=11 Hz, 1H) 6.33 (d, J=11 Hz, 1H), 7.6–8.1 (4H).

REFERENCE EXAMPLE 14

To a solution of 1.7 mg of 22-p-tolylsulfonyl-9,10-secocholesta-5,7,10(19)-triene-1α,3β,24,25 -tetraol in 2 ml of methanol was added 0.25 g of disodium hydrogen phosphate, followed by the addition of 0.8 g of 5% sodium amalgam, and the mixture was stirred under argon atmosphere for 30 minutes. The reaction mixture was diluted with methanol and the insoluble matter was filtered off and washed with methanol. The filtrate and washings were combined and concentrated under reduced pressure. Purification of the residue by silica gel thin layer chromatography gave 0.7 mg of 9,10-secocholesta-5,7,10(19)-triene-1α,3β,24,25-tetraol.

$^1$H NMR spectrum (90 MHz) $\delta_{TMS}$CDCl$_3$: 0.57 (s, 3H), 1.13 (s, 6H), 3.25 (m, 1H), 4.1–4.5 (2H), 4.89 (br. s, 1H), 5.25 (br. s, 1H), 6.05 (d, J=11 Hz, 1H), 6.30 (d, J=11 Hz, 1H).

UV spectrum (ethanol) λmax: 265 nm.
Mass spectrum (FD) : 432 (M+).

EXAMPLE 43

In 2 ml of tetrahydrofuran was dissolved 83 mg of 20-methyl-1α,3β-bis(t-butyldimethylsilyloxy)-21-phenylsulfonylpregna-5,7-diene and the solution was cooled in a dry ice-acetone bath under argon atmosphere. Then, 0.4 ml of a lithium diisopropylamide solution prepared from 2 ml of a 1.5N hexane solution of butyllithium and 0.4 ml of diisopropylamine in 10 ml of tetrahydrofuran was added and the mixture was stirred at −30° C. for 30 minutes. The mixture was again cooled in a dry ice-acetone bath and a solution of 150 mg of 4-(2-bromoethyl)-2,2,4-trimethyl-1,3-dioxolane in 1 ml of tetrahydrofuran was added. The resulting mixture was stirred at −20° C. for 5 hours. A saturated aqueous solution of ammonium chloride was added to the reaction mixture, the mixture was allowed to warm to ambient temperature. Diethyl ether was added to the reaction mixture, the organic layer was separated, and the aqueous layer was extracted with diethyl ether. The organic layer was combined, washed in sequence with an aqueous solution of sodium hydrogen carbonate and an aqueous solution of sodium chloride, then dried over sodium sulfate and concentrated. Purification of the residue by silica gel column chromatography gave 72 mg of 1α,3β-bis(t-butyldimethylsilyloxy)-25,26-isopropylidenedioxy-22-phenylsulfonylcholesta-5,7-diene.

$^1$H NMR spectrum (90 MHz) $\delta_{TMS}$CDCl$_3$: 0.04 (s, 3H), 0.07 (s, 6H), 0.11 (s, 3H), 0.70 (s, 3H), 0.88 (s, 9H), 0.90 (s, 9H), 0.92 (d, J=6 Hz, 3H), 1.01 (s, 3H), 1.28 (s, 3H), 1.40 (s, 6H), 3.5–3.9 (3H), 4.1–4.5 (2H), 5.41 (m, 1H), 5.66 (m, 1H), 7.6–8.1 (5H).

EXAMPLE 44

In 400 ml of diethyl ether was dissolved 72 mg of 1α,3β-bis(t-butyldimethylsilyloxy)-25,26-isopropylidenedioxy-22-phenylsulfonylcholesta-5,7-diene and the solution was cooled in an ice bath while argon gas was passing through the solution. This solution was irradiated with ultraviolet light for 5 minutes using a 400 W high pressure mercury lamp. The reaction mixture was concentrated under reduced pressure and the residue was purified by silica gel column chromatography to give 13.2 mg of 1α,3β-bis(t-butyldimethylsilyloxy)-25,26-isopropylidenedioxy-22-phenylsulfonyl-9,10-secocholesta-5(10),6,8-triene. This was dissolved in 3 ml of ethanol and the solution was heated under reflux under argon atmosphere for 2 hours. After cooling, the reaction mixture was concentrated under reduced pressure. Purification by silica gel thin layer chromatography gave 8.4 mg of 1α,3β-bis(t-butyldimethylsilyloxy)-25,26-isopropylidenedioxy-22-phenylsulfonyl-9,10-secocholesta-5,7,10(19)-triene having the physical characteristics shown below.

$^1$H NMR spectrum (90 MHz) $\delta_{TMS}$CDCl$_3$: 0.05 (s, 12H), 0.56 (s, 3H), 0.87 (s, 18H), 0.99 (d, J=6 Hz, 3H), 1.30 (s, 3H), 1.45 (s, 6H), 3.5–3.9 (3H), 4.1–4.5 (2H), 4.87 (br. s, 1H), 5.18 (br. s, 1H), 6.05 (d, J=11 Hz, 1H), 6.30 (d, J=11 Hz, 1H), 7.6–8.1 (5H).

EXAMPLE 45

To 8.4 mg of 1α,3β-bis(t-butyldimethylsilyloxy)-25,26-isopropylidenedioxy-22-phenylsulfonyl-9,10-secocholesta-5,7,10(19)-triene was added 2 ml of an acetic acid-water-tetrahydrofuran mixture (3:1:1 by volume). The resulting mixture was stirred at room temperature for 12 hours. The reaction mixture was neutralized by addition of an aqueous solution of sodium hydrogen carbonate and then concentrated under reduced pressure. Purification of the residue by silica gel thin layer chromatography gave 5.1 mg of 22-phenylsulfonyl-9,10-secocholesta-5,7,10(19)-triene-1α,3β,25, 26-tetraol.

$^1$H NMR spectrum (90 MHz) $\delta_{TMS}$CDCl$_3$: 0.60 (s, 3H), 1.01 (d, J=6 Hz, 3H), 1.30 (s, 3H), 3.4–4.0 (3H), 4.1–4.6 (2H), 4.93 (br. s, 1H), 5.32 (br. s, 1H), 6.01 (d, J=11 Hz, 1H), 6.29 (d, J=11 Hz, 1H), 7.6–8.1 (5H).

REFERENCE EXAMPLE 15

To a solution of 5.1 mg of 22-phenylsulfonyl-9,10-secocholesta-5,7,10(19)-triene-1α,3β, 25,26-tetraol in 2 ml of methanol was added 0.25 g of disodium hydrogen phosphate, followed by the addition of 0.8 g of 5% sodium amalgam, and the mixture was stirred under argon atmosphere for 30 minutes. The reaction mixture was diluted with methanol and the insoluble matter was filtered off and washed with methanol. The filtrate and washings were combined and concentrated under reduced pressure. Purification of the residue by silica gel thin layer chromatography gave 2.2 mg of 9,10-secocholesta-5,7,10(19)-triene-1α,3β,25,26-tetra-ol.

$^1$H NMR spectrum (90 MHz) $\delta_{TMS}$CDCl$_3$: 0.60 (s, 3H), 0.99 (d, J=6 Hz, 3H), 1.34 (s, 3H), 3.4–3.9 (2H), 4.1–4.6 (2H), 5.00 (br. s, 1H), 5.32 (br. s, 1H), 6.03 (d, J=11 Hz, 1H), 6.33 (d, J=11 Hz, 1H).

UV spectrum (ethanol) λmax: 264 nm.
Mass spectrum (FD) : 432 (M+).

REFERENCE EXAMPLE 16

A solution of 82 mg of 20-methyl-1α,3β-diacetoxy-21-p-toluenesulfonyloxypregna-5,7-diene in 1.5 ml of diethyl ether was added dropwise, at −50° C. to −60° C., to a diethyl ether solution of diisoamylcopper lithium prepared from 100 mg of cuprous iodide and 0.9 ml of a 1.1N diethyl ether solution of isoamyllithium in 2 ml of diethyl ether. After stirring at −30° C. for 1 hour, the reaction mixture was poured into a cold aqueous solution of ammonium chloride, followed by extraction with diethyl ether. The extract was washed with 10% aqueous ammonia, water and an aqueous solution of sodium chloride, dried over sodium sulfate and concentrated. The residue was dissolved in 1 ml of methanol, 10 mg of potassium carbonate was added, and the mixture was stirred at ambient temperature for 10 hours. Thereafter, the isolation and purification procedure of Reference Example 8 was repeated to give 35 mg of cholesta-5,7-diene-1α,3β-diol, whose $^1$H NMR spectrum was identical with that obtained in Reference Example 8.

REFERENCE EXAMPLE 17

A solution of 99 mg of 20-methyl-1α,3β-bis(t-butyldimethylsilyloxy)-21-p-toluenesulfonyloxypregna-5,7-diene in 2 ml of diethyl ether was added dropwise, at −50° C. to −60° C., to a diethyl ether solution of iodide and 0.9 ml of a 1.1N diethyl ether solution of isoamyllithium in 2 ml of diethyl ether. After stirring at −30° C. for 1 hour, the reaction mixture was poured into a cold aqueous solution of ammonium chloride, followed by extraction with diethyl ether. The extract was washed with 10% aqueous ammonia, water and an aqueous solution of sodium chloride, dried over sodium sulfate and concentrated. The residue was dissolved in 2 ml of tetrahydrofuran, 1 ml of a 40% aqueous solution of tetra-n-butylammonium fluoride was added, and the mixture was stirred at room temperature for 6 hours. The reaction mixture was diluted with water and extracted with methylene chloride. The extract was washed with an aqueous solution of sodium chloride, dried over sodium sulfate and concentrated. The residue was washed with cold ethyl acetate to give 45 mg of cholesta-5,7-diene-1α,3β-diol, whose $^1$H NMR spectrum was identical with that obtained in Reference Example 8.

REFERENCE EXAMPLE 18

A solution of 78 mg of 20-methyl-1α,3β-bis(methoxymethoxy)-21-p-toluenesulfonyloxypregna-5,7-diene in 2 ml of diethyl ether was added dropwise, at −50° C. to −60° C., to a diethyl ether solution of diisoamylcopper lithium prepared from 100 mg of cuprous iodide and 0.9 ml of a 1.1N diethyl ether solution of isoamyllithium in 2 ml of diethyl ether. After stirring at −30° C. for 1 hour, the reaction mixture was poured into a cold aqueous solution of ammonium chloride, followed by extraction with diethyl ether. The extract was washed with 10% aqueous ammonia, water and an aqueous solution of sodium chloride, dried over sodium sulfate and concentrated. The residue was dissolved in 1 ml of methanol, 1 ml of 1N hydrochloric acid was added, and the mixture was stirred at room temperature for 10 hours. The reaction mixture was diluted with water and extracted with methylene chloride. The extract was washed with an aqueous solution of sodium hydrogen carbonate and an aqueous solution of sodium chloride, dried over sodium sulfate and concentrated. The residue was washed with cold ethyl acetate to give 37 mg of cholesta-5,7-diene-1α,3β-diol, whose $^1$H NMR spectrum was identical with that obtained in Reference Example 8.

EXAMPLE 46

To a solution of 29 mg of 20-methyl-1α,3β-bis(methoxycarbonyloxy)-21-phenylsulfinylpregna-5,7-diene in 1 ml of methanol was added 0.5 ml of a 30% aqueous solution of hydrogen peroxide and the mixture was stirred at ambient temperature for 6 hours. The reaction mixture was diluted with water and the methanol was distilled off under reduced pressure. The residue was extracted with methylene chloride, the extract was washed with an aqueous solution of sodium thiosulfate, water and an aqueous solution of sodium chloride, dried over sodium sulfate and concentrated. The residue was purified by silica gel column chromatography to give 13 mg of 20-methyl-1α,3β-bis(methoxycarbonyloxy)-21-phenylsulfonylpregna-5,7-diene, whose $^1$H NMR spectrum was identical with that obtained in Example 5.

EXAMPLE 47

To a solution of 53 mg of 20-methyl-1α,3β-bis-(methoxycarbonyloxy)-21-p-toluenesulfonyloxypregna-5,7-diene in 5 ml of acetone was added 120 mg of sodium iodide and the mixture was heated under reflux for 4 hours. The reaction mixture was cooled, then the acetone was distilled off under reduced pressure, water was added to the residue, and the resulting mixture was extracted with diethyl ether. The extract was washed with water, an aqueous solution of sodium thiosulfate, water, an aqueous solution of sodium hydrogen carbonate and an aqueous solution of sodium chloride, then dried over sodium sulfate and concentrated. Purification of the residue by silica gel column chromatography gave 38 mg of 21-iodo-20-methyl-1α,3β-bis(methoxycarbonyloxy)-pregna-5,7-diene.

$^1$H NMR spectrum (90 MHz) $\delta_{TMS}$CDCl$_3$: 0.76 (s, 3H), 1.02 (s, 3H), 1.03 (d, J=6 Hz, 3H), 3.12 (m, 2H), 3.75 (s, 3H), 3.77 (s, 3H), 4.6–5.2 (2H), 5.40 (m, 1H), 5.65 (m, 1H)

EXAMPLE 48

A mixture of 71 mg of 21-iodo-20-methyl-1α,3β-bis-(methoxycarbonyloxy)pregna-5,7-diene, 80 mg of sodium benzenesulfinate and 3 ml of dimethylformamide was stirred at 40° C. for 7 hours. The reaction mixture was subjected to the same isolation and purification procedure in Example 5 to give 42 mg of 20-methyl-1α,3β-bis(methoxycarbonyloxy)-21-phenylsulfonylpregna-5,7-diene, whose $^1$H NMR spectrum was identical with that obtained in Example 5.

EXAMPLE 49

To a solution of 51 mg of 20-methyl-1α,3β-diacetoxy-21-p-toluenesulfonyloxypregna-5,7-diene in 5 ml of acetone was added 100 mg of lithium bromide and the mixture was heated under reflux for 10 hours. The same isolation and purification procedure in Example 47 gave mg of 21-bromo-20-methyl-1α,3β-diacetoxypregna-5,7-diene, whose $^1$H NMR spectrum was identical with that obtained in Example 12.

EXAMPLE 50

The procedure of Example 49 was repeated except that 64 mg of 20-methyl-1α,3β-bis(t-butyldimethylsilyloxy)-21-p-toluenesulfonyloxypregna-5,7-diene was used in lieu of 51 mg of 20-methyl-1α,3β-diacetoxy-21-p-toluenesulfonyloxypregna-5,7-diene to give 49 mg bromo-20-methyl-1α,3β-bis(t-butyldimethylsilyloxy)-pregna-5,7-diene, whose $^1$H NMR spectrum was identical with that obtained in Example 13.

EXAMPLE 51

The procedure of Example 49 was repeated except that 48 mg of 20-methyl-1α,3β-bis(methoxymethoxy)-21-p-toluenesulfonyloxypregna-5,7-diene was used in lieu of 51 mg of 20-methyl-1α,3β-diacetoxy-21-p-toluenesulfonyloxypregna-5,7-diene to give 31 mg of 21-bromo-20-methyl-1α,3β-bis(methoxymethoxy)pregna-5,7-diene, whose $^1$H NMR spectrum was identical with that obtained in Example 14.

EXAMPLE 52

The procedure of Example 11 was repeated except that 85 mg of methyl 1α,3β-bis(t-butyldimethylsilyloxy)pregna-5,7-diene-20-carboxylate was used in lieu of 70 mg of methyl 1α,3β-bis(methoxycarbonyloxy)pregna-5,7-diene-20-carboxylate to give 55 mg of 1α,3β-bis(t-butyldimethylsilyloxy)-20-methylpregna-5,7-diene-21-ol, whose $^1$H NMR spectrum was identical with that obtained in Example 9.

EXAMPLE 53

The procedure of Example 11 was repeated except that 65 mg of methyl 1α,3β-bis(methoxymethoxy)pregna-5,7-diene-20-carboxylate was used in lieu of 70 mg of methyl 1α,3β-bis(methoxycarbonyloxy)pregna-5,7-diene-20 carboxylate to give 47 mg of 1α,3β-bis(methoxymethoxy)-20methylpregna-5,7-diene-21-ol, whose $^1$H NMR spectrum was identical with that obtained in Example 10.

EXAMPLE 54

The procedure of Example 28 was repeated except that 280 mg of isoamyl bromide was used in lieu of 150 mg of isovaleraldehyde to give 31 mg of 1α,3β-bis(methoxycarbonyloxy)-22-phenylsulfonylcholesta-5,7-diene.

$^1$H NMR spectrum (90 MHz) $\delta_{TMS}$CDCl$_3$: 0.65 (s, 3H), 0.8-1.2 (12H), 3.50 (m, 1H), 3.65 (s, 3H), 3.69 (s, 3H), 4.4-4.9 (2H), 5.32 (m, 1H), 5.60 (m, 1H), 7.6-8.1 (5H).

EXAMPLE 55

The procedure of Example 29 was repeated except that 31 mg of 1α,3β-bis(methoxycarbonyloxy)-22-phenylsulfonylcholesta-5,7-diene was used in lieu of 28 mg of 1α,3β-bis(methoxycarbonyloxy)-22-phenylsulfonylcholesta-5,7-dien-23-ol to give 4.2 mg of 1α,3β-bis(methoxycarbonyloxy)-22-phenylsulfonyl-9,10-secocholesta-5,7,10(19)-triene.

$^1$H NMR spectrum (90 MHz) $\delta_{TMS}$CDCl$_3$: 0.57 (s, 3H), 0.91 (d, J=7 Hz, 9H), 3.52 (m, 1H), 3.67 (s, 3H), 3.70 (s, 3H), 4.5-5.1 (3H), 5.30 (br. s, 1H), 5.97 (d, J=11 Hz, 1H), 6.28 (d, J=11 Hz, 1H), 7.6-8.1 (5H).

EXAMPLE 56

The procedure of Example 30 was repeated except that 4.2 mg of 1α,3β-bis(methoxycarbonyloxy)-22-phenylsulfonyl-9,10-secocholesta-5,7,10(19)-triene was used in lieu of 4.8 mg of 1α,3β-bis(methoxycarbonyloxy)-22-phenylsulfonyl-9,10-secocholesta-5,7,10(19)-trien-23-ol to give 2.8 mg of 22-phenylsulfonyl-9,10-secocholesta-5,7,10(19)-triene-1α,3β-diol.

$^1$H NMR spectrum (90 MHz) $\delta_{TMS}$CDCl$_3$: 0.60 (s, 3H), 0.95 (d, J=6 Hz, 9H), 3.53 (m, 1H), 4.2-4.6 (2H), 4.99 (br. s, 1H), 5.15 (br. s, 1H), 5.94 (d, J=11 Hz, 1H), 6.28 (d, J=11 Hz, 1H), 7.6-8.1 (5H).

REFERENCE EXAMPLE 19

The procedure of Reference Example 10 was repeated except that 2.8 mg of 22-phenylsulfonyl-9,10-secocholesta-5,7,10(19)-triene-1α,3β-diol was used in lieu of 3.2 mg of 22-phenylsulfonyl-9,10-secocholesta-5,7,10(19)-triene-1α,3β-triol to give 1.2 mg of 9,10-secocholesta-5,7,10(19)-triene-1α,3β-diol.

$^1$H NMR spectrum (90 MHz) $\delta_{TMS}$CDCl$_3$: 0.58 (s, 3H), 0.96 (d, J=6 Hz, 9H), 4.1-4.5 (2H), 5.02 (br. s, 1H), 5.30 (br. s, 1H), 6.05 (d, J=11 Hz, 1H), 6.35 (d, J=11 Hz, 1H).

UV spectrum (ethanol) λmax: 264 nm.
Mass spectrum (FD) : 400 (M+).

INDUSTRIAL APPLICABILITY

In accordance with the invention, there are provided novel steroid compounds useful as intermediates for the synthesis of vitamin D$_3$ derivatives having a hydroxyl group at the 1α-position.

We claim:

1. A pregnane derivative of the formula

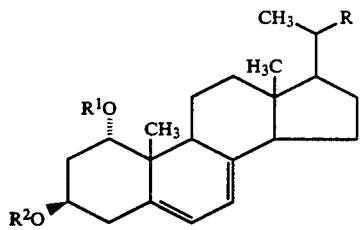

wherein R$^1$ and R$^2$ each is a hydrogen atom; trialkylsilyl group; an acyl group selected from the group consisting of acetyl, propionyl, butyryl, isobutyryl, valeryl, isovaleryl, pivaloyl, benzoyl, monochloroacetyl, and trifluoroacetyl; an alkoxycarbonyl group; or an alkoxyalkyl group and R is a group of the formula —CH$_2$—X, a carboxyl group or an alkyl carboxyl group or a C$_{7-10}$ aryl carboxyl group, X being a hydroxyl group, an acyloxyl group selected from the group consisting of acetoxyl, propionyloxyl, butyryloxyl, isobutryloxyl, valeryloxyl, isovaleryloxy, pivaloyloxyl, benzoyloxyl, monochloroacetoxyl and trifluoroacetoxyl, a lower alkoxycarbonyloxyl group, a trisubstituted silyloxyl group selected from the group consisting of trialkylsilyloxyl and C$_{67}$-diarylalkylsilyloxyl, an alkoxymethoxyl group an alkyl-substituted alkoxymethoxyl group, a 2-oxacycloalkylyloxyl group, a benzyloxyl group a p-nitrobenzyloxyl group, a triphenylmethoxyl group, a dimethoxytrityloxyl group, a halogen atom, an alkylsulfonyloxy group, a C$_{67}$-arylsulfonyloxy group, a C$_{67}$-arylsulfinyl group, an alkylsufinyl group, a pyridylsulfinyl group, a C$_{67}$-arylsulfonyl group, an alkylsulfonyl group or a pyridylsulfonyl group.

2. A pregnane derivative according to claim 1, said pregnane derivative having the formula

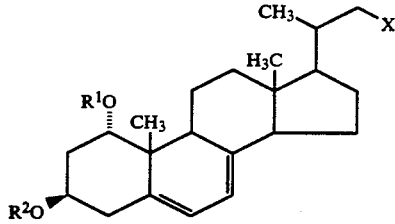

wherein R$^1$, R$^2$ and X are as defined in claim 1.

3. A pregnane derivative according to claim 1, said pregnane derivative having the formula

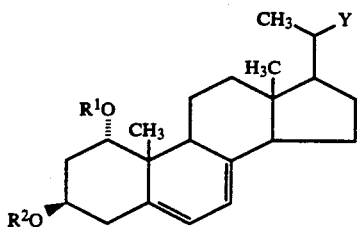

wherein R$^1$ and R$^2$ are as defined in claim 1 and Y is a carboxyl group or a protected carboxyl group.

* * * * *